(12) United States Patent
Hendricks

(10) Patent No.: US 12,268,866 B2
(45) Date of Patent: Apr. 8, 2025

(54) SYSTEMS AND METHODS FOR IMPLANTABLE ELECTRODES WITH FEEDBACK FOR APPLICATION OF ELECTRIC FIELD THERAPY WITHIN THE BODY

(71) Applicant: Dignity Health, San Francisco, CA (US)

(72) Inventor: Benjamin Hendricks, San Francisco, CA (US)

(73) Assignee: Dignity Health, San Francisco, CA (US)

(*) Notice: Subject to any disclaimer, the term of this patent is extended or adjusted under 35 U.S.C. 154(b) by 0 days.

(21) Appl. No.: 18/551,765

(22) PCT Filed: Apr. 11, 2022

(86) PCT No.: PCT/US2022/024265
§ 371 (c)(1),
(2) Date: Sep. 21, 2023

(87) PCT Pub. No.: WO2022/217144
PCT Pub. Date: Oct. 13, 2022

(65) Prior Publication Data
US 2024/0091525 A1   Mar. 21, 2024

Related U.S. Application Data

(60) Provisional application No. 63/173,410, filed on Apr. 10, 2021.

(51) Int. Cl.
*A61N 1/05* (2006.01)
*A61N 1/372* (2006.01)
*A61N 1/378* (2006.01)

(52) U.S. Cl.
CPC ........... *A61N 1/05* (2013.01); *A61N 1/37247* (2013.01); *A61N 1/37252* (2013.01); *A61N 1/3785* (2013.01)

(58) Field of Classification Search
CPC .. A61N 1/05; A61N 1/37247; A61N 1/37252; A61N 1/3785
See application file for complete search history.

(56) References Cited

U.S. PATENT DOCUMENTS 9,539,430 B2 * 1/2017 Mishra ................... A61N 1/371
2002/0062143 A1 5/2002 Baudino et al.
(Continued)

FOREIGN PATENT DOCUMENTS

WO 2021067873 A1 4/2021

OTHER PUBLICATIONS

Patent Cooperation Treaty, International Search Report and Written Opinion, International Application No. PCT/US2022/024265, date of mailing Jul. 18, 2022, 11 pages.
(Continued)

*Primary Examiner* — Mark W. Bockelman
(74) *Attorney, Agent, or Firm* — Polsinelli PC

(57) ABSTRACT

An implantable electrode system includes a controller device to treat apply electric field therapy (EFT) to a target structure according to specific anatomical properties of the target structure. The system enables selective association of contacts of the implantable electrode system with one or more target locations of varying tissue types within the body for application and measurement of EFT. The one or more target locations are associated with one or more anticipated tissue parameters that the implantable electrode system uses to apply and update waveform parameters to modulate EFT application from each respective contact to the one or more target locations.

24 Claims, 20 Drawing Sheets

(56) References Cited

U.S. PATENT DOCUMENTS

| | | |
|---|---|---|
| 2011/0160800 A1 | 6/2011 | Dawant et al. |
| 2011/0257697 A1* | 10/2011 | Jarverud .............. A61B 5/7239 |
| | | 607/18 |
| 2018/0185651 A1* | 7/2018 | Astrom .............. A61N 1/36185 |
| 2019/0117973 A1* | 4/2019 | Schmidt ............. A61N 1/37247 |
| 2019/0232057 A1 | 8/2019 | Perryman et al. |
| 2019/0336776 A1 | 11/2019 | Cowan et al. |
| 2019/0358450 A1 | 11/2019 | Lo et al. |
| 2020/0001096 A1 | 1/2020 | Zhang et al. |
| 2020/0179690 A1 | 6/2020 | Schepis et al. |
| 2022/0266044 A1* | 8/2022 | Sorenson ............. A61N 1/3968 |

OTHER PUBLICATIONS

European Patent Office, Extended European Search Report, Application No. 22785592.1, Aug. 16, 2024, 6 pages.

\* cited by examiner

SYSTEMS AND METHODS FOR IMPLANTABLE ELECTRODES WITH FEEDBACK FOR APPLICATION OF ELECTRIC FIELD THERAPY WITHIN THE BODY

CROSS-REFERENCE TO RELATED APPLICATIONS

This is a PCT application that claims benefit to U.S. Provisional Patent Application Ser. No. 63/173,410 filed Apr. 10, 2021, which is herein incorporated by reference in its entirety.

FIELD

The present disclosure generally relates to electric field therapy, and in particular, to a system and associated method for feedback-guided application of electric field therapy through internally-implanted electrodes.

BACKGROUND

Alternating electric field application has been explored as cancer therapy for almost two decades with a growing body of literature supporting its use for a variety of cranial and extra-cranial malignancies. This growing body of evidence has focused on transcutaneous delivery of alternating electric fields to eventually expose tumors within the body to the electric field. A very limited number of studies have embarked on an implantable solution, however most of these lack a means of feedback or measurement of the field being generated. The value remains apparent that delivery of alternating electric fields to tumor cells has a notable impact on cell function which is preferential over the impact on native cells.

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures do not limit the scope of the claims.

DETAILED DESCRIPTION

The present disclosure provides systems and associated methods for an implantable electrode system including a controller device to treat corporeal tumors with unique stimulation parameters to accommodate disruption of tumor specific cell division with anatomically appropriate electrode configurations. The system enables selective association of contacts of the implantable electrode system with one or more target locations within the body, including various parenchymal structures of varying tissue types. The one or more target locations are associated with one or more anticipated tissue parameters that the controller device uses to apply and update waveform parameters to modulate application of electric field therapy (EFT) from each respective contact to the one or more target locations.

To permit generation of therapeutic electric fields around and within parenchymal structures of interest, implantation strategies and hardware will vary. For example, renditions of multiple permissibly treated parenchymal structures with EFT are provided herein. Several possible arrangements for application of stimulation are as follows:

(1) Implantation of a "intra-parenchymal" electrode with one or more contacts placed within the parenchymal structure (2) Implantation or adhesion of a "paddle" or "grid" electrode with one or more contacts placed along the surface of the parenchymal structure and held in place using bonding, bio-adhesives, or scaffolds to maintain electrode placement following open or laparoscopic/endoscopic surgical access and placement (3) Implantation or insertion of an "intra-luminal" electrode within an endoluminal space of a parenchymal structure with one or more contacts placed along an endoluminal surface of the parenchymal structure (4) Utilization of an implantable control system housing as a source for stimulation and/or grounding Definitions of some terms within this disclosure are outlined here. In particular, the term "parenchymal structure" defines an organ structure within the body, in particular, a "functional" part of the organ structure. Parenchymal structures can include one or more sub-structures that include parenchymal tissue. The term "stroma structure"

defines a structural or connective component of the organ structure or surrounding the organ structure without specific organ functions such as connective tissue or blood vessels.

Overview

Figure 1:
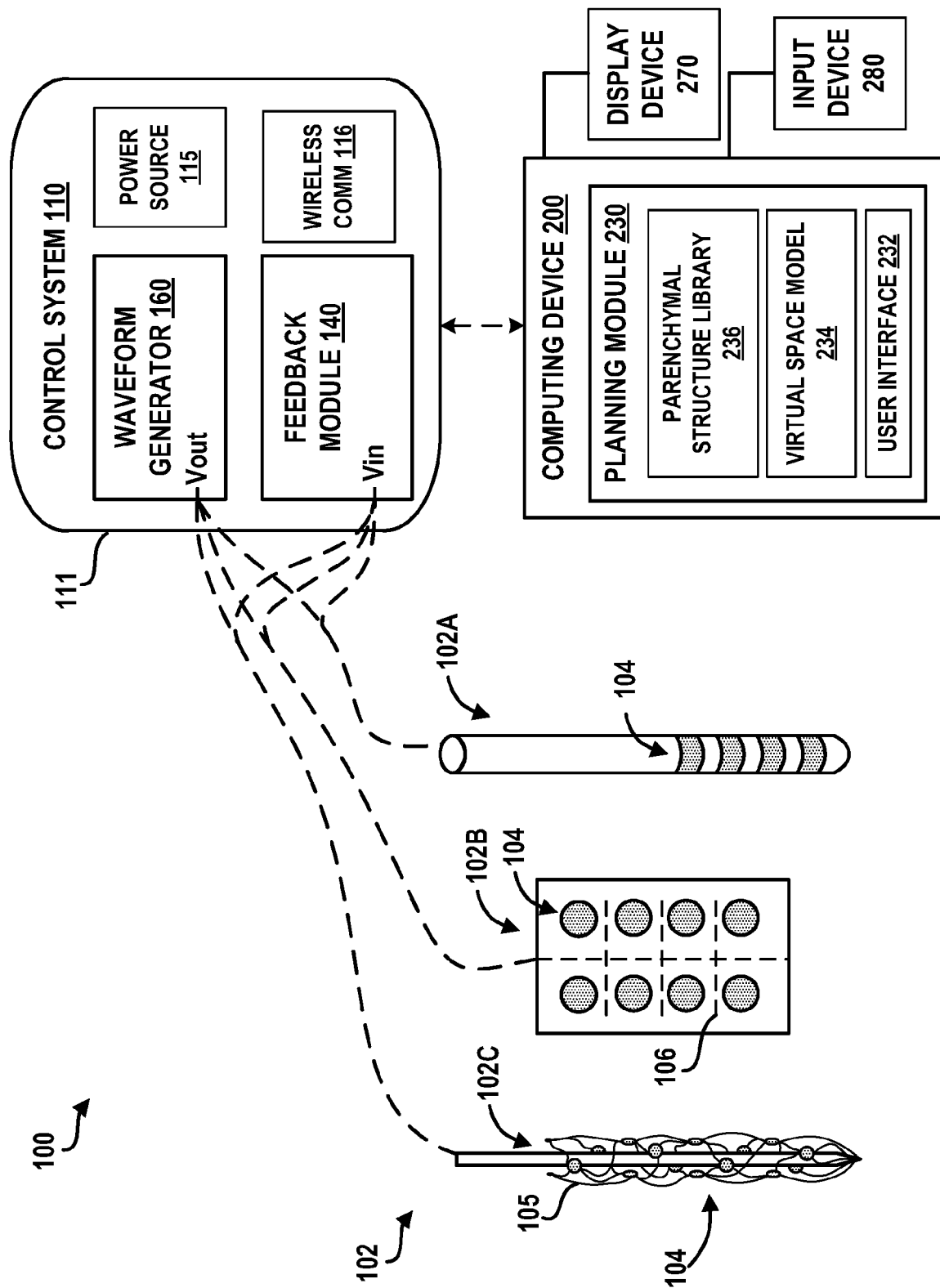
FIG. 1 is a simplified diagram showing an electric field therapy (EFT) system in electrical communication with a computing device for planning and administering parenchymal structure-specific EFT treatment.

Referring to FIG. 1, an example electric field therapy (EFT) system 100 is provided that includes one or more implantable electrodes 102 in electrical communication with a control system 110 for application of EFT treatment to one or more target structures, particularly one or more parenchymal structures and associated stroma structures within the body. In some embodiments, the one or more implantable electrodes 102 can vary in design to enable placement of the one or more implantable electrodes 102 at various locations within and around different parenchymal and stroma structures to apply a stimulating waveform to the tissue in accordance with various treatment parameters and tissue properties that are specific to a "target" structure. The control system 110 includes a waveform generator 160 that generates a stimulating waveform to be applied to the target structure through the one or more implantable electrodes 102 according to the treatment parameters, and further includes a feedback module 140 that incorporates measurable feedback received from the target structure to optimize the applied stimulating waveform. In some embodiments, the control system 110 is implantable within the body, and an implantable housing 111 of the control system 110 can optionally act as an implantable electrode 102 that applies a stimulating waveform or provides a grounding reference point for the one or more implantable electrodes 102. The control system 110 communicates with an external computing device 200 that includes a computer-implemented planning module 230 that determines one or more treatment parameters to be applied to a target structure including a parenchymal structure and associated stroma structures through the one or more implantable electrodes 102 and configures the implantable EFT system 100 accordingly. In particular, the computer-implemented planning module 230 provides: (1) a user interface 232 for receipt of one or more structure selections indicative of a target structure; (2) visual illustrations in the form of a virtual space model 234 of the target structure; and (3) a determination of one or more treatment parameters to govern EFT treatment applied through the implantable EFT system 100 based on known properties of the target structure maintained within a parenchymal structure library 236.

Further, hardware components for the control system 110 are located within the implantable housing 111, which can optionally act as an electrode and provide one or more contacts along a surface of the implantable housing 111, and/or can act as a grounding component for the one or more implantable electrodes 102 in electrical communication with the control system 110. As shown and as discussed above, the control system 110 can include the waveform generator 160 that provides stimulating waveforms to the one or more implantable electrodes 102 for application to tissue based on the one or more treatment parameters that are specific to the target structure. Further, the control system 110 can include the feedback module 140 that receives feedback from the tissue in the form of resultant voltage measurements from the one or more implantable electrodes 102 to optimize the stimulating waveforms applied to the tissue, with modulatory feedback also being governed by the one or more treatment parameters that are specific to the target structure. The control system 110 can include a power source 115 that provides requisite power to the waveform generator 160 and the feedback module 140. In some embodiments, the control system 110 can include a wireless communication component 116 that receives control inputs from the computer-implemented planning module 230 and transmits the measurable feedback back to the computer-implemented planning module 230 for optimization and analysis.

The computer-implemented planning module 230 can communicate with a display device 270 that enables a practitioner to view and interact with the user interface 232 including display of the virtual space model 234. As shown, the computer-implemented planning module 230 can communicate with an input device 280 to receive input from the practitioner though the user interface 232, the input including one or more structure selections indicative of a target structure for application of EFT. The computer-implemented planning module 230 can consult a parenchymal structure library 236 to identify one or more tissue parameters of the target structure based on the one or more structure selections, which can be used to determine one or more treatment parameters to be applied and can also be used to modulate the one or more treatment parameters based on received post-implantation feedback from the control system 110. Further, the computer-implemented planning module 230 can generate or otherwise display a virtual space model 234 that includes anatomical virtual model objects representative of the one or more structure selections, which can be modeled based on expected/standard anatomy or patient-specific anatomy obtained through radiographic imaging. In some embodiments, the virtual space model 234 can also include one or more virtual model electrode objects of the one or more implantable electrodes 102 of the implantable EFT system 100 that can be superimposed over the anatomical virtual model objects to show example placement of the one or more implantable electrodes 102 within and around the one or more parenchymal structure selections; placement of the virtual model electrode objects can be computer-generated, or clinician controlled.

Electrodes

FIG. 1 illustrates variations of the one or more implantable electrodes 102 of the implantable EFT system 100. Each implantable electrode 102 of the one or more implantable electrodes 102 includes one or more contacts 104 located along a surface of the respective implantable electrode 102 that contacts tissue and applies the stimulating waveform provided by the waveform generator 160 of the control system 110. In a preferred embodiment, at least one of the one or more contacts 104 of the implantable EFT system 100 is operable to receive one or more measurements resultant of the stimulating waveform from within the tissue, which is incorporated by the feedback module 140 of the control system 110 to modulate the stimulating waveform provided by the waveform generator 160 of the control system 110. In some embodiments, each individual implantable electrode 102 including associated stimulating waveform parameters can be selected according to a target structure that the individual implantable electrode 102 is intended to interface with. For instance, a target structure may include a parenchymal structure including multiple types of tissue and sub-structures therein, as well as one or more surrounding stroma structures that are targeted for EFT treatment to prevent or reduce metastatic spread of a cancerous region. A resultant electrode configuration of the implantable EFT system 100 that would be applied to the target structure would need to account for the variation in tissue types and sub-structures of the parenchymal structure and would also need to be applied to the one or more surrounding stroma structures. A solution can involve implantation of the plurality of implantable electrodes 102 featuring more than one design type and a plurality of contacts 104 for each respective implantable electrode 102, each respective implantable electrode 102 being engaged at variable positions along, within and around the target structure. Each contact 104 of the plurality of contacts 104 can be individually recognized by the control system 110 and the computer-implemented planning module 230 and can apply a unique stimulating waveform to the tissue based on the properties of the specific tissue type and location that the contact 104 interfaces with. Further, the control system 110 and/or the computer-implemented planning module 230 can assign a "stimulating" role or "measuring" role to each individual contact 104 of the plurality of contacts 104 for applying the stimulating waveform and measuring the resultant effect within the tissue to be incorporated as feedback.

In one example, FIG. 1 shows an "intra-parenchymal" electrode 102A of the one or more implantable electrodes 102 configured for intra-parenchymal into tissue that includes a plurality of contacts 104 positioned along a length of the intra-parenchymal electrode 102A, each contact 104 of the plurality of contacts 104 being individually configurable by the control system 110. FIG. 1 also illustrates an extra-parenchymal electrode 102B of the one or more implantable electrodes 102 configured for adhesion onto a surface of a parenchymal structure that includes a plurality of contacts 104 positioned along a surface of the extra-parenchymal electrode 102B, each contact 104 of the plurality of contacts 104 being individually configurable by the control system 110. Further, FIG. 1 provides an example "intra-luminal" electrode 102C of the one or more implantable electrodes 102 configured for insertion within a luminal structure (endoluminal space) of a target structure. The intra-luminal electrode 102C similarly includes a plurality of contacts 104 positioned along a length of the intra-luminal electrode 102C, each contact 104 of the plurality of contacts 104 being individually configurable by the control system 110. In some embodiments, the intra-luminal electrode 102C can include a semi-rigid netting 105 that serves a dual-purpose of supporting and connecting the plurality of contacts 104 to the control system 110 and maintaining an open configuration of the endoluminal space. The plurality of contacts 104 contact an interior (intra-luminal) surface of the luminal structure to hold the intra-luminal electrode 102C in place while allowing fluid to pass through the luminal structure so as not to cause a blockage. In some embodiments, the one or more implantable electrodes 102 are modular in size and number of contacts 104. For instance, the intra-parenchymal electrodes 102A or intra-luminal electrodes 102C can be trimmed to an intended length, allowing removal of unused contacts 104 to reduce an invasive profile of the intra-parenchymal electrodes 102A or intra-luminal electrodes 102C. The extra-parenchymal electrodes 102B can each provide a "grid" featuring the plurality of contacts 104 positioned in a grid pattern along a flexible material; the extra-parenchymal electrodes 102B can similarly be cut to size enabling removal of unused contacts 104 and can be manufactured in varying sizes, with contemplated embodiments ranging from a single contact 104 to an array with hundreds of contacts 104. In some embodiments, the extra-parenchymal electrodes 102B can include one or more perforations 106 that aid in conformation to concave or convex surfaces such as those present within organic structures.

Linear electrode arrays such as the intra-parenchymal electrode 102A represent the simplest method of electrode placement with the lowest volumetric capability for electric field coverage. Stereotactic placement of intra-parenchymal electrodes 102A or intra-luminal electrodes 102C usually cannot be accomplished within most parenchymal structures using optical guidance (as is typically employed in the setting of many cranial procedures) given the lack of a rigid boundary to fixate the tissue; therefore, computed tomography or x-ray guided placement of intra-parenchymal electrodes 102A or intra-luminal electrodes 102C are a viable option for ensuring correct placement of intra-parenchymal electrodes 102A or intra-luminal electrodes 102C. This would mirror a technique of similar procedures such as fine needle aspiration or biopsy of lung lesions. The larger "paddle" or "grid" electrodes such as extra-parenchymal electrode 102B would require open surgical access to the target structure to permit placement. Some parenchymal structures or anatomical regions may permit access through laparoscopic or endoscopic techniques for electrode placement. For some anatomical regions, as mentioned above, it may be advantageous for the implantable housing 111 of the control system 110 including the waveform generator 160 and feedback module 140 to also serve as an implantable electrode 102 for electric field generation.

Computer-Implemented Planning Module

Determination of appropriate treatment parameters for a given tumor type (for example, breast, lung, pancreatic, liver, etc.) with subtyping investigations yielding specific treatment parameters (for example, pulmonary adenocarcinoma vs. squamous cell carcinoma vs. large cell carcinoma vs. small cell lung cancer in the case of a lung cancer) are necessary to permit effective electric field treatment. The computer-implemented planning module 230 incorporates this information into a treatment planning workflow to enable practitioners to select appropriate treatment parameters based on the target structure and associated tissues.

Treatment parameters can include:
  applied voltage or current amplitude to be applied through each contact 104 based on tissue properties of the structure selection (available in parenchymal structure library 236)
  stimulating waveform frequency to be applied through each contact 104 based on tissue properties of the structure selection (available in parenchymal structure library 236)
  configurations (i.e., position relative to ROI and organization relative to one another including pairing) of contacts 104 based on the structure selection
  types of implantable electrodes 102 to be used based on the structure selection (recommendation available in parenchymal structure library 236)

Following selection of an appropriate treatment parameter for each respective contact 104 of the one or more implantable electrodes 102, the implantable EFT system 100 can be configured to measure aspects of the resultant electric field within defined target zones (as measured by one or more implantable electrodes 102 within the region of interest) with feedback-mediated modulation of stimulating waveform parameters applied through the waveform generator 160. Further, phase-shifting pairing between contacts 104 can be implemented to permit accentuation of the electric field generated between anode/cathode electrode pairs. For instance, application of the stimulating waveform at complimentary phases (e.g., 180 degrees out-of-phase with one another) can maximize the EFT treatment being applied to the target structure and/or modulate an orientation of the applied EFT treatment while reducing power consumption. This technique can be used to optimize the generated electric field across larger distances within the target structure.

In some embodiments, the computer-implemented planning module 230 maintains the parenchymal structure library 236 that includes data for a plurality of parenchymal structures and corresponding sub-regions, tissue types, and nearby stroma structures that are associated with each respective parenchymal structure, as well as medically accepted treatment parameters, expected volumes and electrical properties of each respective sub-region and tissue type. The computer-implemented planning module 230 provides a user interface 232 for the practitioner to interact with when planning treatment and maintains virtual space models 234 for each structure selection which can be viewed through the user interface 232. As shown in the example user interface 232 of FIG. 2A, when determining treatment parameters, computer-implemented planning module 230 receives one or more structure selections 239. In particular, computer-implemented planning module 230 prompts the practitioner to enter one or more "primary" structure selections, which can indicate one or more parenchymal structures selected as "primary" target structures. For instance, a first primary structure selection can be a liver, and a second primary structure selection can be a gallbladder, both of which are considered target parenchymal structures. As shown, the structure selections 239 can include n primary structure selections. Based on each primary structure selection, computer-implemented planning module 230 prompts the practitioner to enter one or more associated "secondary" structure selections which can include: (1) one or more parenchymal sub-structures located within the target parenchymal structure(s) having one or more inherent tissue types based on the parenchymal sub-structure; and/or (2) one or more stroma structures associated with the target parenchymal structure(s) having one or more inherent tissue types based on the stroma structure. Continuing the example, if the first parenchymal structure selected as a "primary" structure selection is the liver, then available parenchymal sub-structures can include a right lobe, a left lobe or other parenchymal sub-structures therein and available stroma structures can include a hepatic duct, falciform ligament, or other non-parenchymal stroma structures associated with the liver, each parenchymal sub-structure or stroma structure having an inherent tissue type with defined dielectric and volumetric properties.

Figure 2A:
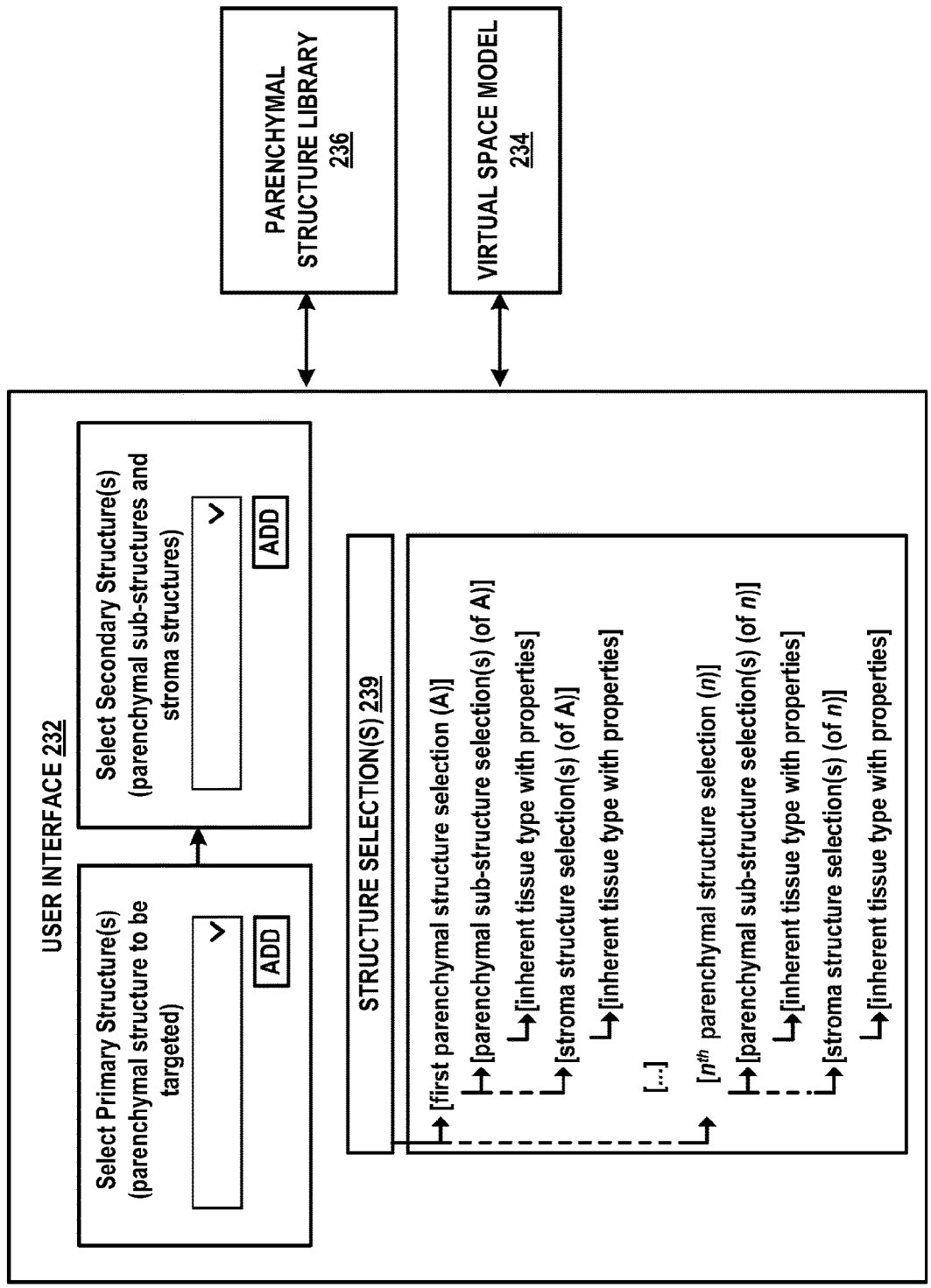
FIGS. 2A and 2B are simplified diagrams showing an example user interface of a computer-implemented planning module of the EFT system of FIG. 1.
Figure 2B:
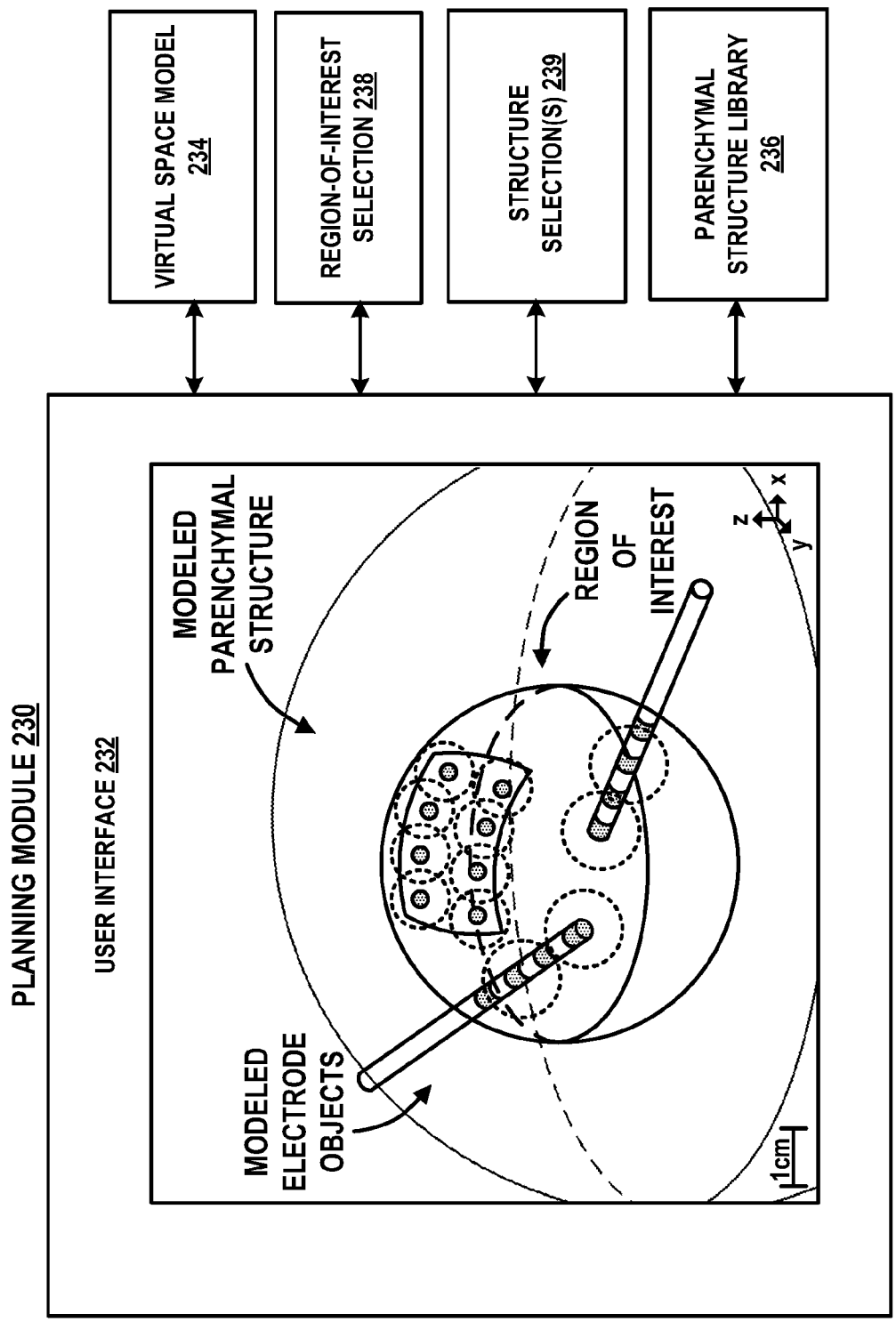

Further, as shown in the example user interface 232 of FIG. 2B, the computer-implemented planning module 230 can provide a viewer to view the virtual space model 234 featuring a modeled parenchymal structure selected through the example user interface 232 of FIG. 2A, which can also include one or more modeled electrode objects that can be superimposed along the modeled parenchymal structure for viewing and analysis by the practitioner. In some embodiments, the computer-implemented planning module 230 can also receive a region of interest selection 238 through the user interface 232 that can indicate a volumetric region of interest within the virtual space model 234 including a tumor region and/or a surrounding region to be targeted. The computer-implemented planning module 230 can also receive one or more EFT threshold parameters for the region-of interest that indicate minimum and/or maximum threshold values associated with magnitude and/or orientation of the electric field that need to be applied to the region of interest.

Figure 3:
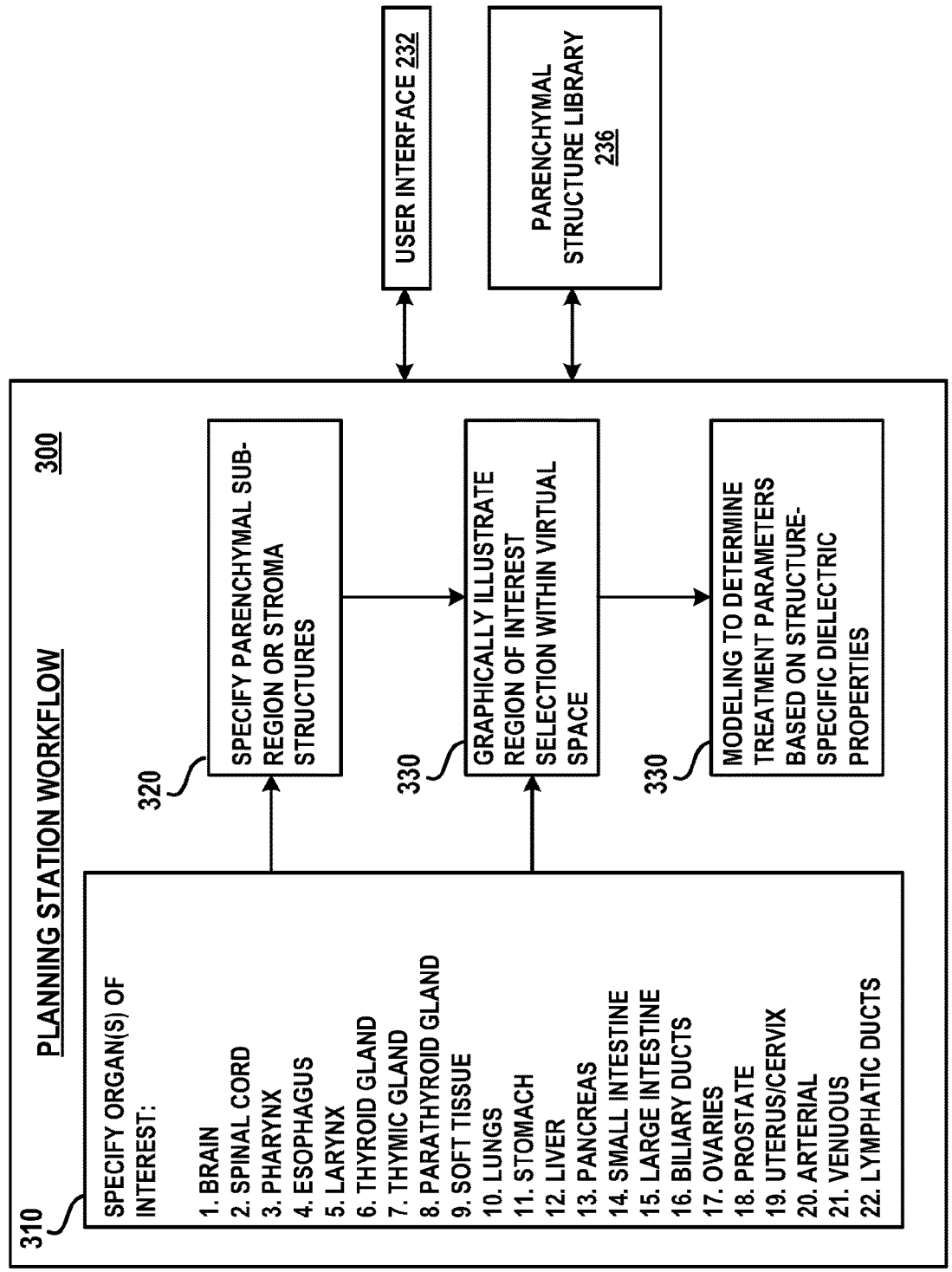
FIG. 3 is a simplified diagram showing an example planning station workflow of the computer-implemented planning module for receiving one or more structure selections representative of a target structure.

Referring to FIG. 3, a simplified diagram 300 is illustrated that provides an example planning station workflow of the computer-implemented planning module 230 for receiving one or more structure selections 239 representative of the target structure from a practitioner, providing an illustration featuring the resultant virtual space model 234 that includes anatomical virtual model objects representative of the one or more structure selections 239, and determination of appropriate treatment parameters based on the one or more structure selections 239. As shown, at block 310, the computer-implemented planning module 230 receives a primary structure selection representative of the target structure through the user interface 232, the details of which are present in the parenchymal structure library 236. A non-limiting example listing of parenchymal structures that can be selected as the primary structure selection is provided here:

1) Brain
2) Spinal Cord
3) Pharynx
4) Esophagus
5) Larynx
6) Thyroid Gland
7) Thymic Gland
8) Parathyroid Gland
9) Soft Tissue
10) Lungs
11) Stomach
12) Liver
13) Pancreas
14) Small Intestine
15) Large Intestine
16) Biliary Ducts
17) Ovaries
18) Prostate
19) Uterus/Cervix
20) Arterial
21) Venous
22) Lymphatic Ducts It should be noted that the computer-implemented planning module 230 can optionally accept one or more custom inputs for alternative areas of the body or parenchymal structures that are not initially provided.

At block 320, the computer-implemented planning module 230 receives one or more secondary structure selections including parenchymal sub-structures and/or stroma structures based on the primary structure selection provided at block 310. As discussed above, the one or more "secondary" structure selections can include: (1) one or more parenchymal sub-structures located within the target parenchymal structure(s) having one or more inherent tissue types with defined dielectric and volumetric properties based on the parenchymal sub-structure; and/or (2) one or more stroma structures associated with the target parenchymal structure(s) having one or more inherent tissue types with defined dielectric and volumetric properties based on the stroma structure. The parenchymal structure library 236 maintains a corpus of sub-regions, sub-structures, tissue types, nearby parenchymal and stroma structures with associated expected positions, expected volumes, and expected tissue properties including dielectric properties for each parenchymal structure. In some embodiments, based on the primary structure selection, the computer-implemented planning module 230 can retrieve one or more options for the one or more secondary parenchymal structure selections from the parenchymal structure library 236 and display them to the practitioner for selection. For example, consider that parenchymal structure #9 from the above listing corresponding with "Soft Tissue" is the primary structure selection provided by the practitioner. Since "Soft Tissue" is a broad, encompassing term, the computer-implemented planning module 230 receives a secondary structure selection such as an anatomical region that "Soft Tissue" may be a part of, which can include soft tissue of the head, arms, torso, legs, or another anatomical region that includes soft tissue. In another example, if a different primary structure selection was received at block 310, such as the thyroid gland, then at block 320 the computer-implemented planning module 230 prompts the practitioner to specify one or more sub-regions (e.g., right lobe, left lobe, isthmus, etc.), and/or surrounding stroma structures specific to the primary structure selection (e.g., nearby lymph nodes, trachea, connective tissue, arteries, etc.) that the practitioner also wants to target to prevent and/or halt metastatic spread, and receives the secondary structure selection from the practitioner.

At block 330, based on the structure selection 239 including the primary structure selection(s) indicative of the target structure(s) and the secondary structure selection(s) indicative of sub-structures or stroma structures associated with one or more target structures, the computer-implemented planning module 230 can provide a graphical illustration of the target structure(s) including a region-of-interest such as a tumor target or tumor bed location. The graphical illustration can be a three-dimensional virtual object representative of the target structure(s) within three-dimensional virtual space, such as the virtual space model 234 of FIG. 2B. In some embodiments, the virtual space model 234 is a three-dimensional model object representative of the target structure(s) and can include additional three-dimensional model objects including modeled electrode objects and a modeled region of interest that can include a tumor region, all of which can be displayed at display device 270. The virtual space model 234 can include information from the parenchymal structure library 236, including expected positions, expected volumes, and expected tissue properties for each target structure(s). In some embodiments, the computer-implemented planning module 230 can enable the practitioner to specify the tumor region representative of where the tumor target or tumor bed location is within the three-dimensional virtual space, and can also enable the practitioner to place one or more modeled electrode objects at select locations within the three-dimensional virtual space to provide a visual representation that shows where the one or more implantable electrodes 102 of the implantable EFT system 100 should be placed. Further, in some embodiments, placement of the one or more modeled electrode objects and the region-of-interest within the three-dimensional virtual space can aid in determining treatment parameters based on specified positions of each respective modeled electrode object by providing the expected tissue properties for the target structure(s) at the specified positions within the three-dimensional virtual space. The virtual space model 234 and associated volumetric and electrical properties as stored within the parenchymal structure library 236 can be case-specific and individually derived based on patient imaging, or can be generically formulated based on expected anatomy with expected variations factored in.

At block 340, based on the modeled three-dimensional virtual space, the computer-implemented planning module 230 can optionally aid the practitioner in deciding where the one or more implantable electrodes 102 of the implantable EFT system 100 should be placed relative to the region-of-interest by orienting the one or more modeled electrode objects such that a maximum area of coverage is achieved across the region-of-interest. This can be done through one or more methods including iterative simulation with "sweeping" electrode and contact parameters until an intended threshold of coverage is achieved across the region-of-interest. Further, the computer-implemented planning module 230 can optionally aid the practitioner in determining one or more stimulating waveform parameters for each respective contact 104 of the implantable EFT system 100 by simulating the effects of each respective contact 104 as positioned within the three-dimensional virtual space with "sweeping" stimulating waveform parameters until an intended threshold of coverage is achieved across the region-of-interest. Alternatively, the computer-implemented planning module 230 can employ one or more machine learning models to determine optimal electrode and contact parameters as well as stimulating waveform parameters. Ultimately, the computer-implemented planning module 230 factors in expected volumes and electrical properties of each respective sub-region and tissue type to aid the practitioner in planning EFT treatment to be applied to the target structure by the implantable EFT system 100.

Within the computer-implemented planning module 230, the practitioner can also configure aspects of the control system 110 and the one or more implantable electrodes 102 of the implantable EFT system 100 based on the treatment parameters and the structure selection 239. For instance, the practitioner can assign "stimulating" or "measuring" roles to each respective contact 104 of the one or more implantable electrodes 102 which would affect how each respective contact 104 connects with the control system 110, as contacts 104 configured in a "stimulating" role would be considered "output devices" of the waveform generator 160 and contacts 104 configured in a "measuring" role would be considered "input devices" of the feedback module 140. Further, the computer-implemented planning module 230 can also specify to the waveform generator 160 the waveform parameters to be applied to each respective stimulating contact 104, which may vary between contacts 104 as each respective contact 104 can be assigned to a different location and tissue type within each target structure that requires unique treatment parameters. The computer-implemented planning module 230 can also specify to the feedback module 140 the expected measurement values that should be received by each respective measuring contact 104, which may vary between contacts 104 as each respective contact 104 can be assigned to a different location and tissue type within each target structure. The computer-implemented planning module 230 can also specify to the feedback module 140 how to update one or more applied waveform parameters if a significant disparity exists between the expected measurement values and actual received measurement values, as appropriate corrective action will naturally be affected by the electrical and volumetric properties of each structure selection 239 including sub-structures, tissue types and associated stroma structures.

Control System and Feedback Modulation

Figure 4:
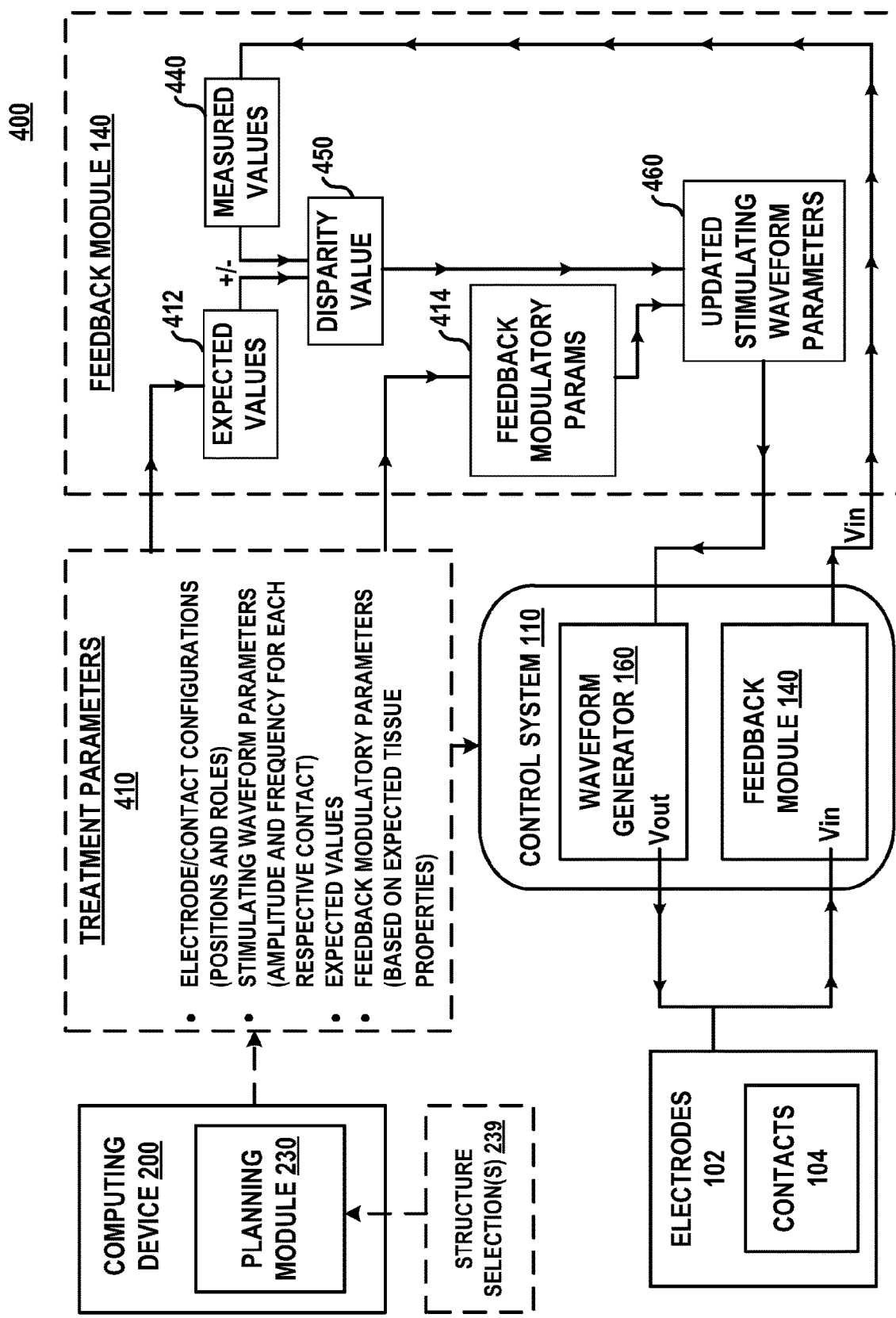
FIG. 4 is a simplified diagram showing feedback modulation of the EFT system of FIG. 1.

Referring to FIG. 4, a simplified data flow diagram 400 illustrates data flow and feedback modulation between the computer-implemented planning module 230 of the computing device 200, the control system 110, and the one or more implantable electrodes 102. Following implantation, the control system 110 uses treatment parameters 410 that are based on the structure selections 239 as provided by the computer-implemented planning module 230 to apply the EFT and modulate feedback. For instance, the waveform generator 160 the control system 110 applies the stimulating waveforms to the tissue through the one or more implantable electrodes 102 according to stimulating waveform parameters as determined by the computer-implemented planning module 230. As discussed above, the stimulating waveform parameters can vary between contacts 104 as each respective contact 104 can be placed at different locations along, within, or around a parenchymal structure which can vary in volumetric and electrical properties. Each respective contact 104 can also assume a "stimulating" or "measuring" role as dictated by the computer-implemented planning module 230 to enable measurement of the resultant effect of the stimulating waveforms within the tissue.

As such, the feedback module 140 can receive one or more measured values 440 from tissue and compare the one or more measured values 440 with one or more expected values 412 provided within the treatment parameters 410 from the computer-implemented planning module 230. If a significant disparity value 450 exists between the one or more measured values 440 and the one or more expected values 412 for a particular measuring contact 104, then the feedback module 140 modifies one or more of the stimulating waveforms accordingly to compensate. As the effects of the stimulating waveform can differ between different tissue types and sub-structures across different parenchymal structures, the feedback module 140 incorporates the electrical and volumetric properties of the structure selection 239 into its modification of the stimulating waveforms. This modification factor can be provided to the feedback module 140 by the computer-implemented planning module 230 as a set of feedback modulatory parameters 414 that are used in combination with the disparity value 450 to determine a set of updated stimulating waveform parameters 460, which are then provided to the waveform generator 160 for application. For instance, according to Ohm's law (J=GE, where J is a vector denoting current density, σ is a scalar value indicative of conductivity, and E is a vector denoting electric field), as conductivity σ across a tissue increases, there is less resistivity ρ (as ρ=1/σ) and therefore voltage declination through the tissue will decrease (as voltage V=IR, where resistance R varies directly with resistivity ρ). With the decrease in voltage, the voltage gradient will also decrease (i.e., electric field magnitude |E|, as Ex=(−dV/dx)). Therefore, for tissues and structures with higher conductivity values, the necessary input voltage should also be higher to enhance the electric field strength across the tissue volume. Conversely, for tissues and structures with lower conductivity values, the necessary input voltage can be lower. For a given intended electric current density J within a particular volume of tissue, the conductivity σ of the tissue affects the strength of the electric field E. The control system 110 can communicate with the computer-implemented planning module 230 to update the treatment parameters 410 over time as additional research is conducted or as parameter modifications are needed.

Parenchymal Structure Treatment Examples
Hepatic Example

Figure 5:
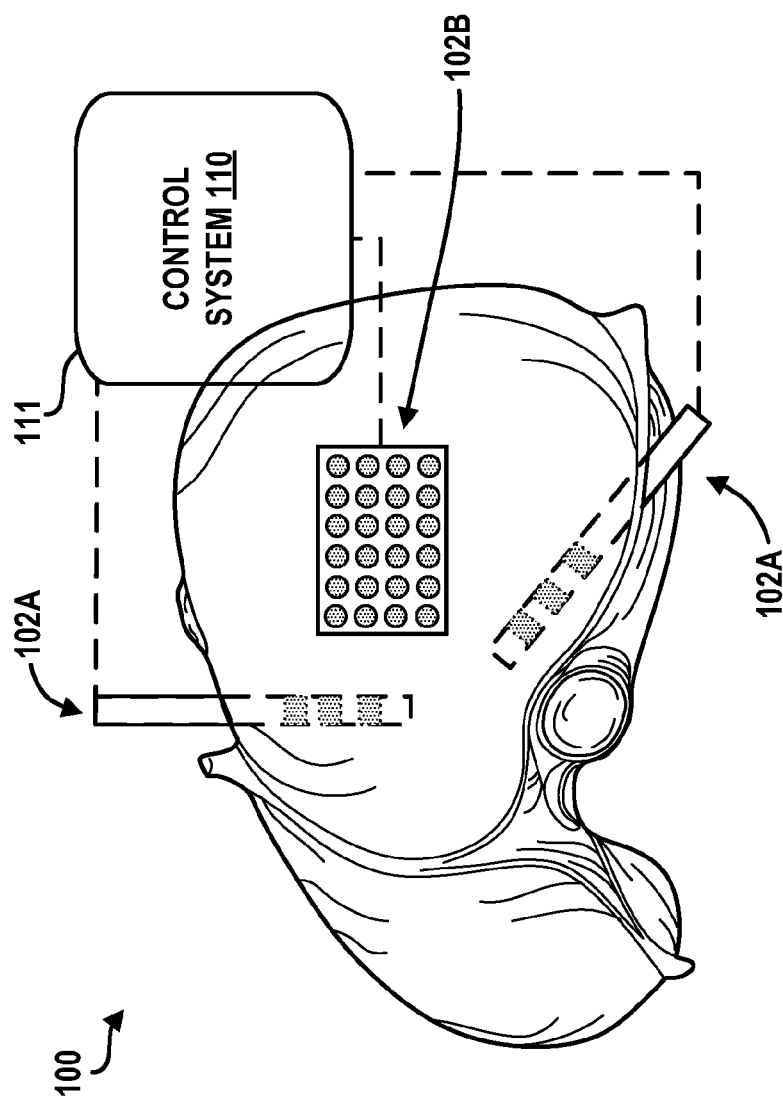
FIG. 5 is a simplified illustration showing application of EFT treatment to a liver by the EFT system of FIG. 1.

FIG. 5 illustrates an example for placement of implantable electrodes 102 of the implantable EFT system 100 relative to a liver as the target structure which include intra-parenchymal electrode arrays 102A positioned within the tissue, extra-parenchymal electrodes 102B placed along the surface of the liver, and additional utilization of the implantable housing 111 of the control system 110 as a source for stimulation. For the liver, the penetration of distribution of electric field will be dependent on the permittivity and electrical conductivity of the tissue. As discussed above, these properties are variable dependent upon the tissue of interest and can also be dependent upon stimulating waveform frequency. For an anticipated application where the stimulating waveform frequency is 150 kHz, the permittivity of the targeted tissue is 6.09E+3 F/m (Farad/meter) and electrical conductivity of the targeted tissue is 9.54E−2 S/m (Siemens/meter) based on empirical data. Using these properties, the computer-implemented planning module 230 (FIG. 2B) can display a virtual model for the liver which can serve as a means for estimation of electric field distribution throughout the liver to determine a necessary implantation strategy to accommodate the region of interest with therapeutic electric field therapy. Given the metastatic capability of hepatic cancer, it may be necessary to implant additional implantable electrodes 102 in adjacent organs, or local or regional lymph node collections to achieve control of regional disease or to prevent or halt progression of further metastatic spread.

Pancreatic Example

Figure 6:
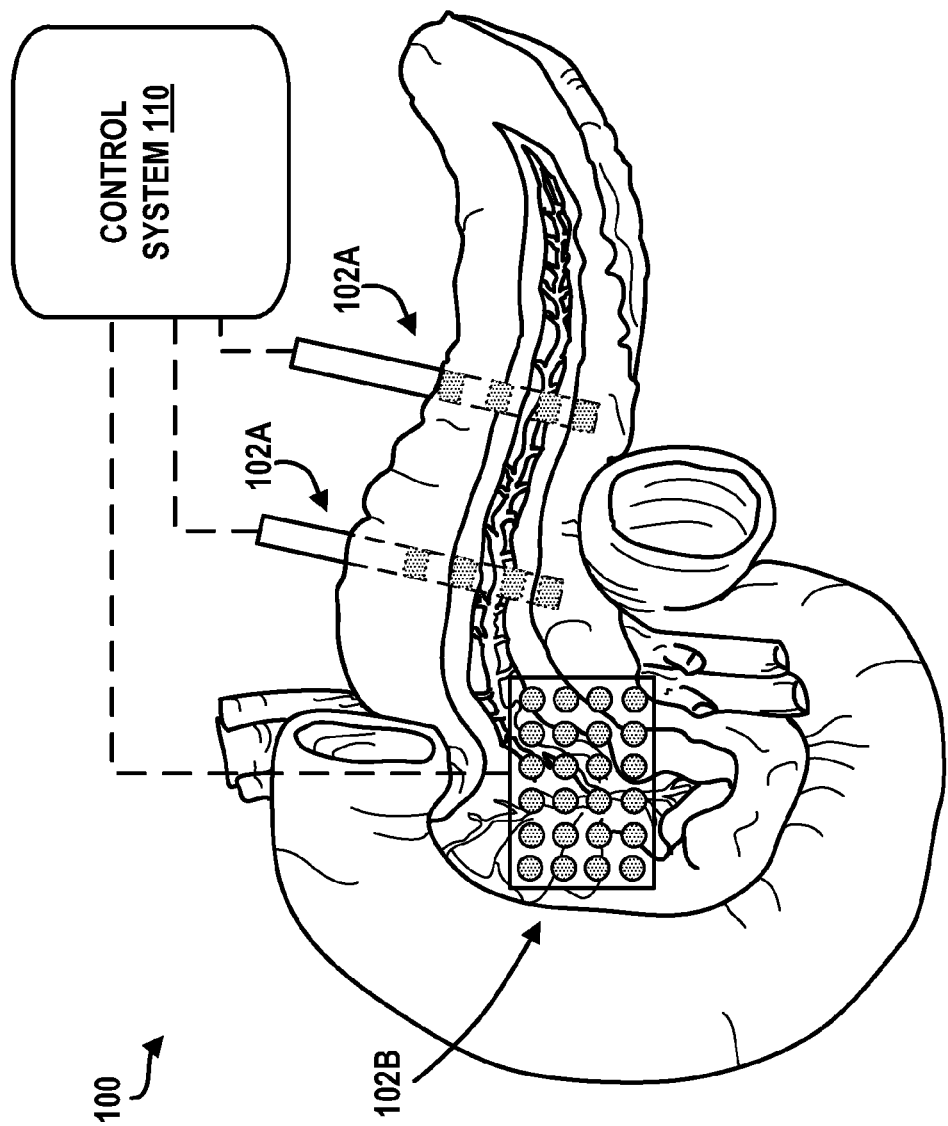
FIG. 6 is a simplified illustration showing application of EFT treatment to a pancreas by the EFT system of FIG. 1.

FIG. 6 illustrates an example for placement of implantable electrodes 102 of the implantable EFT system 100 relative to a pancreas. Pancreatic implantation techniques can involve either intra-parenchymal electrodes 102A or extra-parenchymal electrodes 102B placed on the tissue, similar to that described above for the liver example. For the pancreas, the penetration of distribution of electric field will be dependent on the permittivity and electrical conductivity of the tissue. These properties are variable dependent upon the tissue of interest and frequency of stimulation. For the anticipated application where a waveform frequency is 150 kHz, the resulting permittivity of the tissue is 3.01E+3 F/m and electrical conductivity of the tissue is 5.40E−1 S/m based on empirical data. Using these properties, the computer-implemented planning module 230 (FIG. 2B) can display a virtual model for the pancreas which can and serve as a means for estimation of electric field distribution and thereby necessary implantation strategy to accommodate the region of interest with therapeutic electric field therapy. Given the metastatic capability of pancreatic cancer, it may be necessary to implant additional implantable electrodes 102 in adjacent organs, or local or regional lymph node collections to achieve control of regional disease or to prevent or halt progression of further metastatic spread.

Gastric Example

Figure 7:
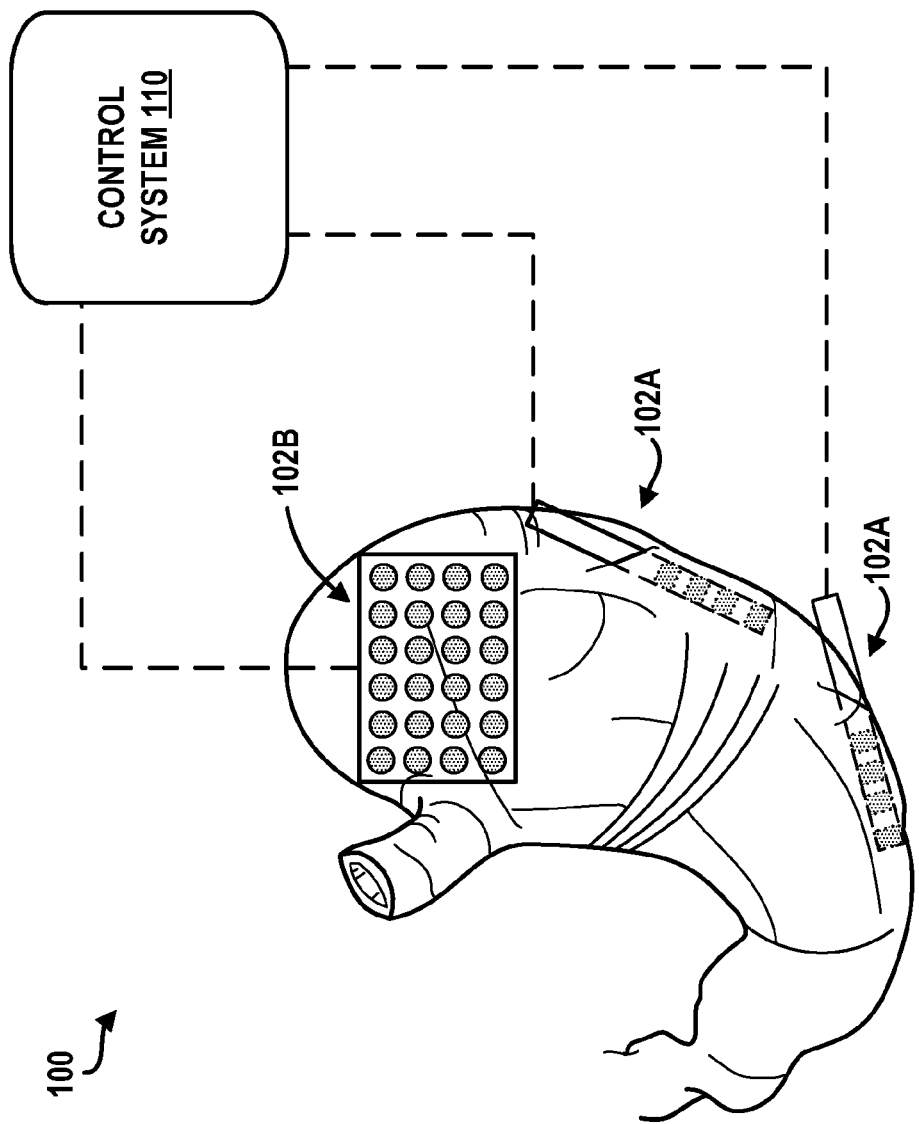
FIG. 7 is a simplified illustration showing application of EFT treatment to a stomach by the EFT system of FIG. 1.

FIG. 7 illustrates an example for placement of implantable electrodes 102 of the implantable EFT system 100 relative to a gastric system. Gastric cancer treatment would involve a slightly different strategy from other non-luminal organs. Given that there is an internal lumen that must be preserved and contains contents that are infectious by nature, it is imperative to preserve the luminal barrier through the implantation and treatment phases. This can be accomplished either through the placement of intra-parenchymal electrodes 102A within the muscular wall of the gastric tissue or through the placement of an extra-parenchymal electrode 102B along the surface of the organ being secured in place by sutures, bonding agents, bio-adhesives, or scaffolds. Anticipated treatment parameters provided to the control system 110 include a waveform frequency of 150 kHz with a minimal goal of 1V/cm electric field gradient within the highest risk region for tumor control or recurrence. For the gastric tissue, the penetration of distribution of electric field will be dependent on the permittivity and electrical conductivity of the tissue. These properties are variable dependent upon the tissue of interest and stimulation waveform frequency. For the anticipated application of 150 kHz, the resulting permittivity will be 2.60E+3 F/m and electrical conductivity would be 5.38E−1 S/m based on empirical data. Given the metastatic capability of gastric cancer, it may be necessary to implant adjacent organs, or local or regional lymph node collections to achieve control of regional disease or to prevent or halt progression of further metastatic spread.

Ovarian Example

Figure 8:
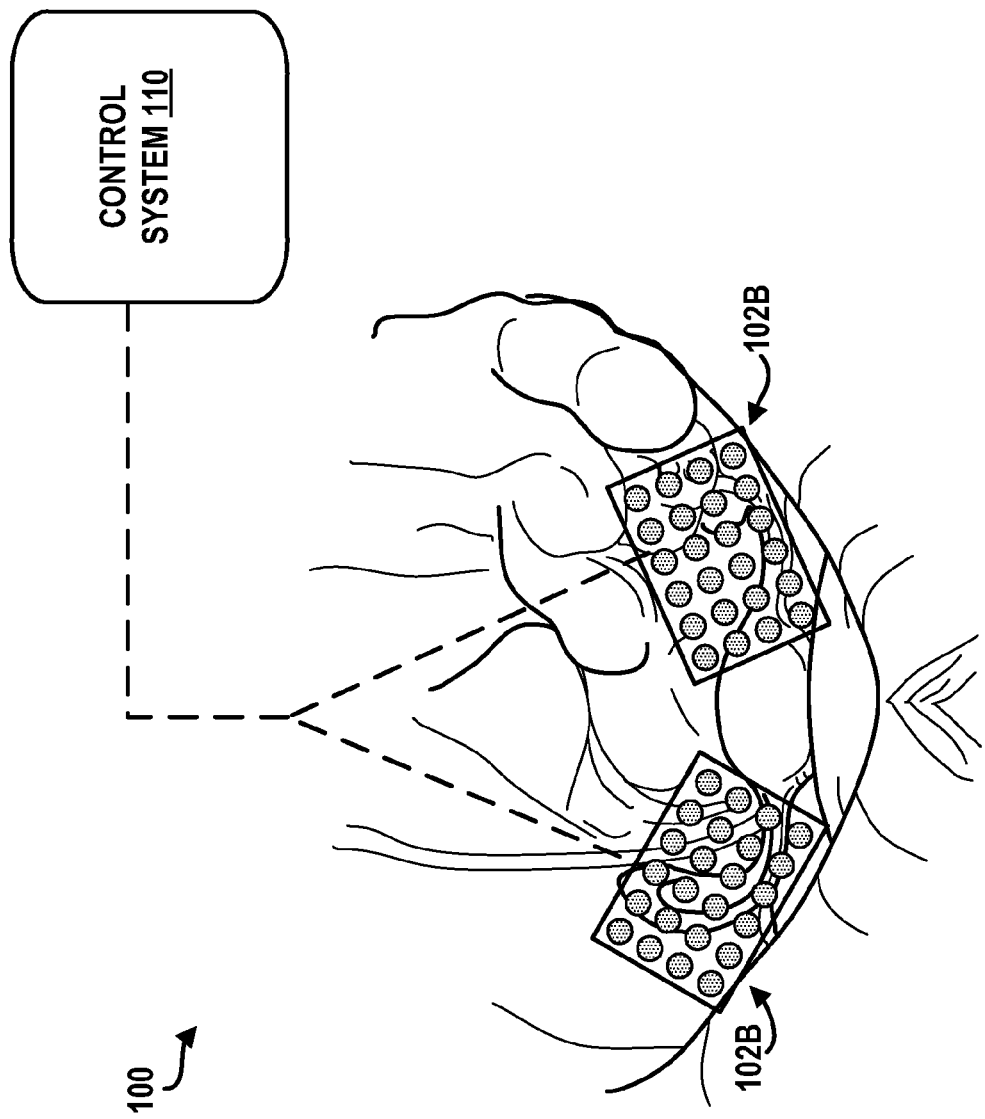
FIG. 8 is a simplified illustration showing application of EFT treatment to an ovarian system by the EFT system of FIG. 1.

FIG. 8 illustrates an example for placement of implantable electrodes 102 of the implantable EFT system 100 relative to an ovarian system, or alternatively a regional pelvic cancer. Ovarian carcinomas are highly malignant cancers with a propensity for metastasis. Current generation standard of care involves a total abdominal hysterectomy and therefore the use case for electric field therapy would be most commonly in a postoperative setting. Similarly, the size of the ovary is such that placement of extra-parenchymal electrodes 102B is likely to be the most effective strategy for implantation alone. The treatment parameters for this application would include a stimulation waveform frequency of 150 kHz with a minimal goal of 1V/cm electric field gradient within the highest risk region for tumor control or recurrence. For ovarian tissue, the penetration of distribution of electric field will be dependent on the permittivity and electrical conductivity of the tissue. These properties are variable dependent upon the tissue of interest and frequency of stimulation. For the anticipated application of 200 kHz the resulting permittivity will be $1.32E+3$ F/m and electrical conductivity would be $3.43E-1$ S/m based on empirical data. Given the metastatic capability of ovarian cancer, it may be necessary to implant adjacent organs, or local or regional lymph node collections to achieve control of regional disease or to prevent or halt progression of further metastatic spread. Notably given the heterogeneity of tissue types adjacent to the ovaries (example: small intestine, large intestine, muscle, bone, adipose, connective tissue) this will require complex modeling to estimate and predict the nuances to implanting this region.

Prostatic Example

Figure 9:
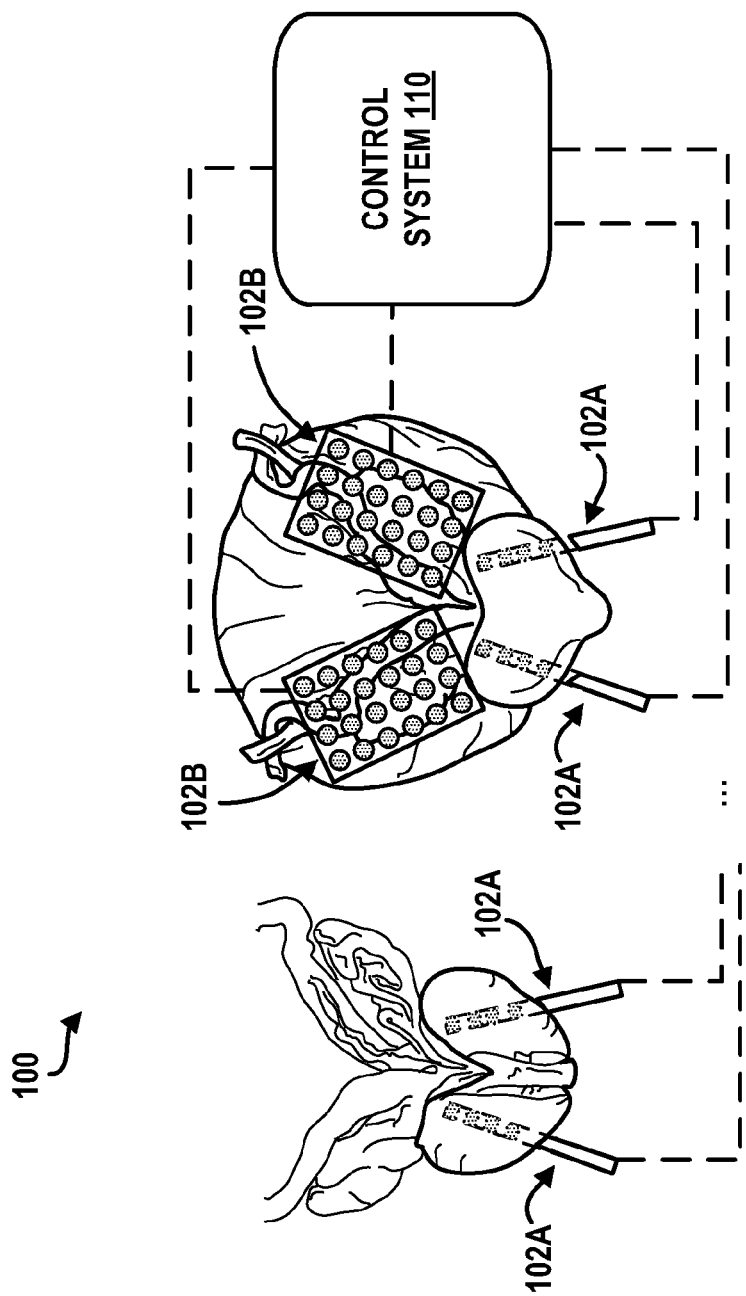
FIG. 9 is a simplified illustration showing application of EFT treatment to a prostatic system by the EFT system of FIG. 1.

FIG. 9 illustrates an example for placement of implantable electrodes 102 of the implantable EFT system 100 relative to a prostatic system. Treatment applications for the prostate organ are likely to involve either treatment of cancer or benign hyperplasia; both have logical roles for electric field therapy. The anticipated parameters for such applications are expected to fall within the stimulating waveform frequency range of 100 kHz-1 MHz, with 100 kHz-200 kHz being most likely. Cancer treatment and treatment of hyperplasia is likely to focus modeling and treatment planning efforts on the prostate tissue given the current standards of care. Therefore, an anticipated application of 100 kHz will result in permittivity of $5.72E+3$ F/m and electrical conductivity of $4.39E-1$ S/m based on empirical data. The anticipated application of 200 kHz will result in permittivity of $5.11E+3$ F/m and electrical conductivity of $4.49E-1$ S/m based on empirical data. Implanting implantable electrodes 102 within the prostate will likely prove to be most effective given the nature of electric field gradients and the small volume of the organ. This can be in the form of intra-parenchymal electrodes 102A or another configuration that enables penetration into tissue. The intra-parenchymal electrodes 102A may be used either independently or in combination with extra-parenchymal electrodes 102B placed along the prostate surface or along neighboring extra-parenchymal regions of loco-regional cancer spread, such as the seminal vesicles (as pictured).

Soft Tissue Examples

Figure 10A:
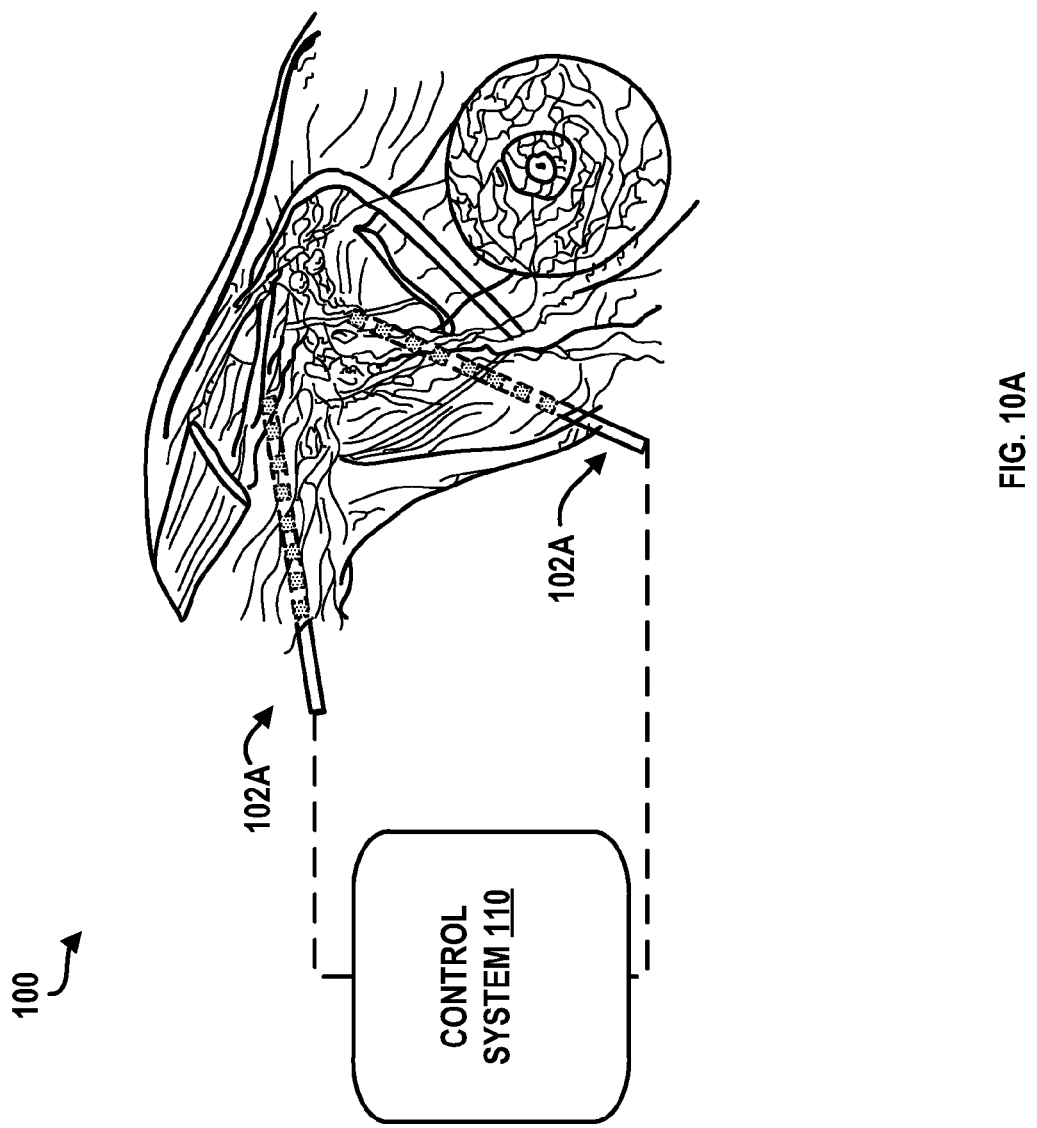
FIGS. 10A-10C are a series of simplified illustrations showing application of EFT treatment to various soft tissues by the EFT system of FIG. 1.
Figure 10C:
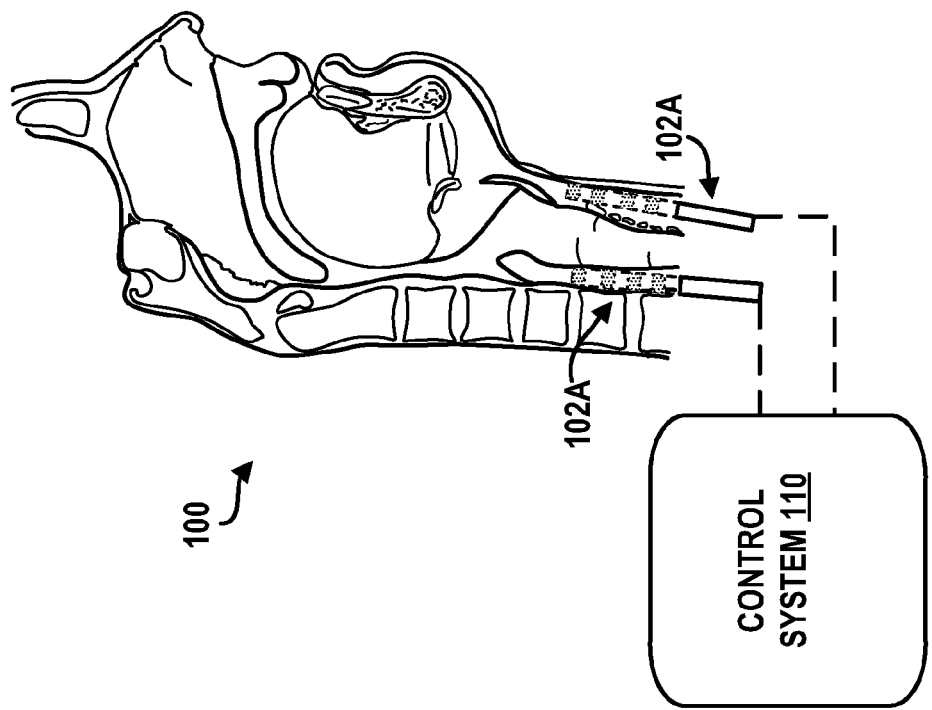
Figure 10B:
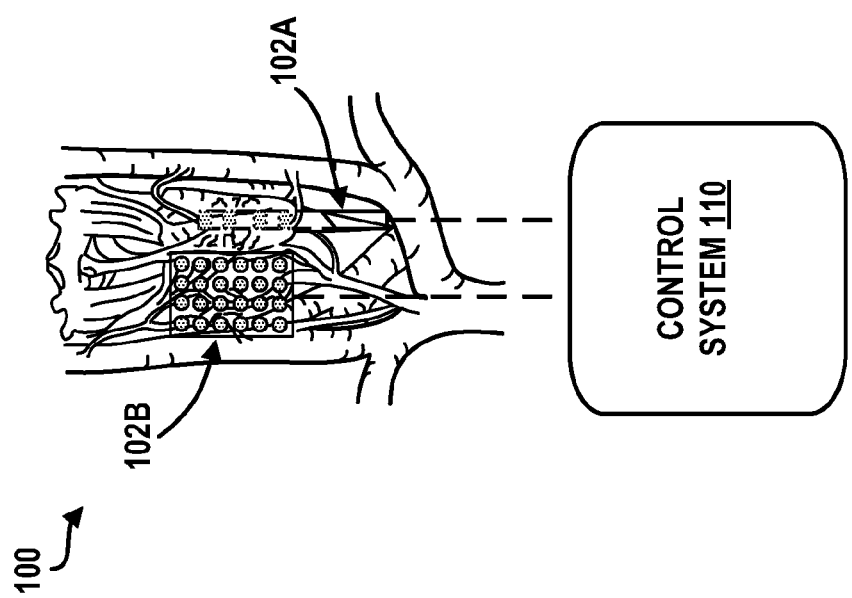

Referring to FIGS. 10A-10C, implantation of implantable electrodes 102 of the implantable EFT system 100 into soft tissue has numerous potential applications, such as lymph node treatment, skin lesion treatments, adipose tissue lesions, lesions within muscle, fascia, bone, peripheral nerve fibers, arteries, and/or veins. Many of these structures are involved in metastatic processes and therefore this implantation strategy has application across a number of pathologies. Depending on the target, the anticipated stimulating waveform frequency for such applications are anticipated to fall within the range of 100 kHz-1 MHz. Melanoma, for example, has evidence of treatment efficacy at a stimulating waveform frequency of 100 kHz. Therefore, an anticipated application of 100 kHz will result in permittivity of $1.12E+3$ F/m and electrical conductivity of $4.51E-1$ S/m based on empirical data. These metrics can be used to model the necessary implantation strategy to treat a skin lesion (i.e. melanoma). More broadly, treatment of lymph nodes within the soft tissue compartments poses potential benefit in the prevention of recurrence and lymphatic spread of tumors (such as breast cancer, treatment of which is illustrated in FIG. 10A). Treatment of such lymph nodes is demonstrated within the axially region. Intra-parenchymal electrodes 102A would permit minimally invasive techniques for implanting within the subcutaneous compartment and achieving region control of lymph node tissues.

Referring to FIGS. 10B and 10C, the soft tissues within the cervical region of the body possess a number of potential targets for electric field therapy: squamous cell carcinoma along the pharynx, esophagus, larynx, thyroid carcinoma, parathyroid carcinoma, thymic carcinoma, and sarcomas. These soft tissue targets are potentially treatable with intra-parenchymal electrodes 102A, extra-parenchymal electrodes 102B, and/or intraluminal electrodes 102C, depending on surgical exposure and the intended target region of coverage. The anticipated parameters for such applications are anticipated to fall within the stimulating waveform frequency range of 100 kHz-1 MHz with the value of 150 kHz being most likely to provide the strongest impact on tumor growth. Effective treatment for the thyroid gland at a stimulating waveform frequency of 150 kHz will result in permittivity of $3.01E+3$ F/m and electrical conductivity of $5.40E-1$ S/m based on empirical data. Effective treatment for the thymus at 150 kHz will result in permittivity of $6.29E+1$ F/m and electrical conductivity of $6.30E-1$ S/m based on empirical data. Effective treatment for the esophagus at 150 kHz will result in permittivity of $2.60E+3$ F/m and electrical conductivity of $5.38E-1$ S/m based on empirical data. With these targets of interest being considered, modeling efforts to inform implant placement will require computational consideration of these variabilities to determine electrode designs and implantation strategies to ensure effective therapy.

Intestinal and Colorectal Example

Figure 11:
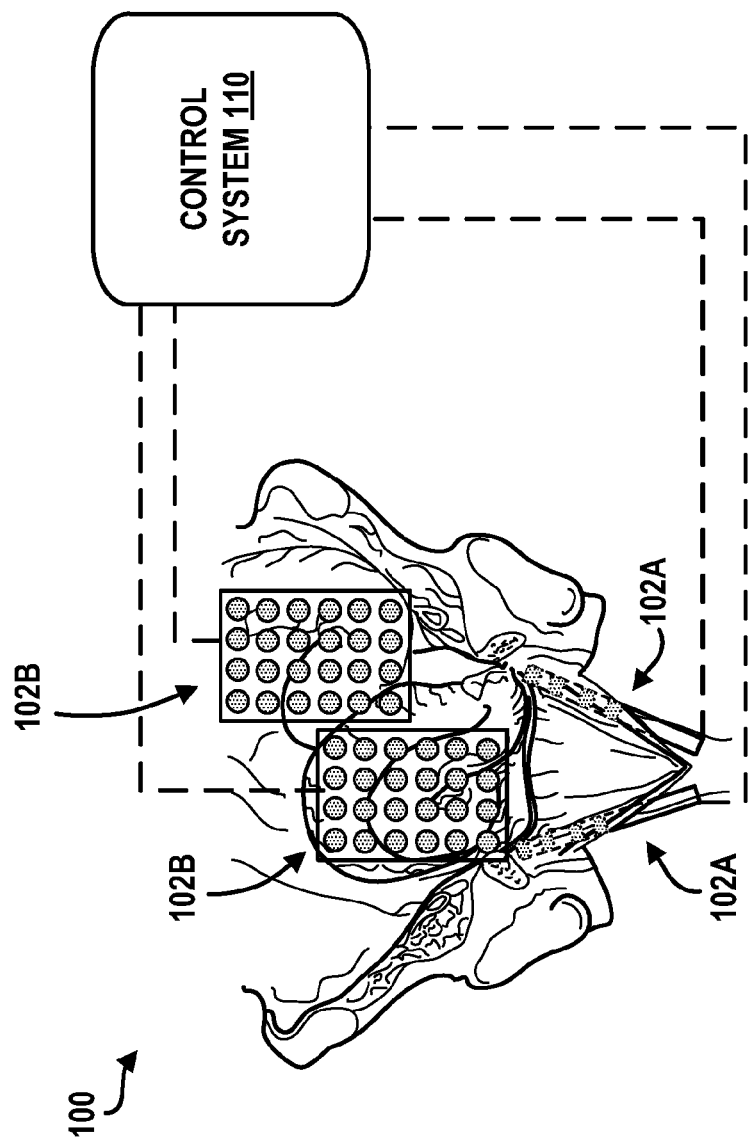
FIG. 11 is a simplified illustration showing application of EFT treatment to a colorectal system by the EFT system of FIG. 1.

FIG. 11 illustrates an example for placement of implantable electrodes 102 of the implantable EFT system 100 relative to an intestinal/colorectal region. Intestinal and colorectal applications for electric field therapy will require implantations over large surface areas. The anticipated parameters for such applications are anticipated to fall within the stimulating waveform frequency range of 100 kHz-1 MHz. The cancer applications for electric field therapy within the realm of intestinal and colorectal anatomy are likely to be post-operative and focus on prevention of disease recurrence and metastatic spread. This will require coverage of regional organs and tissues, overall, a large surface area for treatment coverage. Effective treatment for the large intestine at a stimulating waveform frequency of 150 kHz will result in permittivity of $3.37E+3$ F/m and electrical conductivity of $2.51E-1$ S/m based on empirical data. The modeling calculation necessary for implant placement within these applications will require consideration of electric field spread within multiple tissue types.

Intra-Luminal Example

Figure 12A:
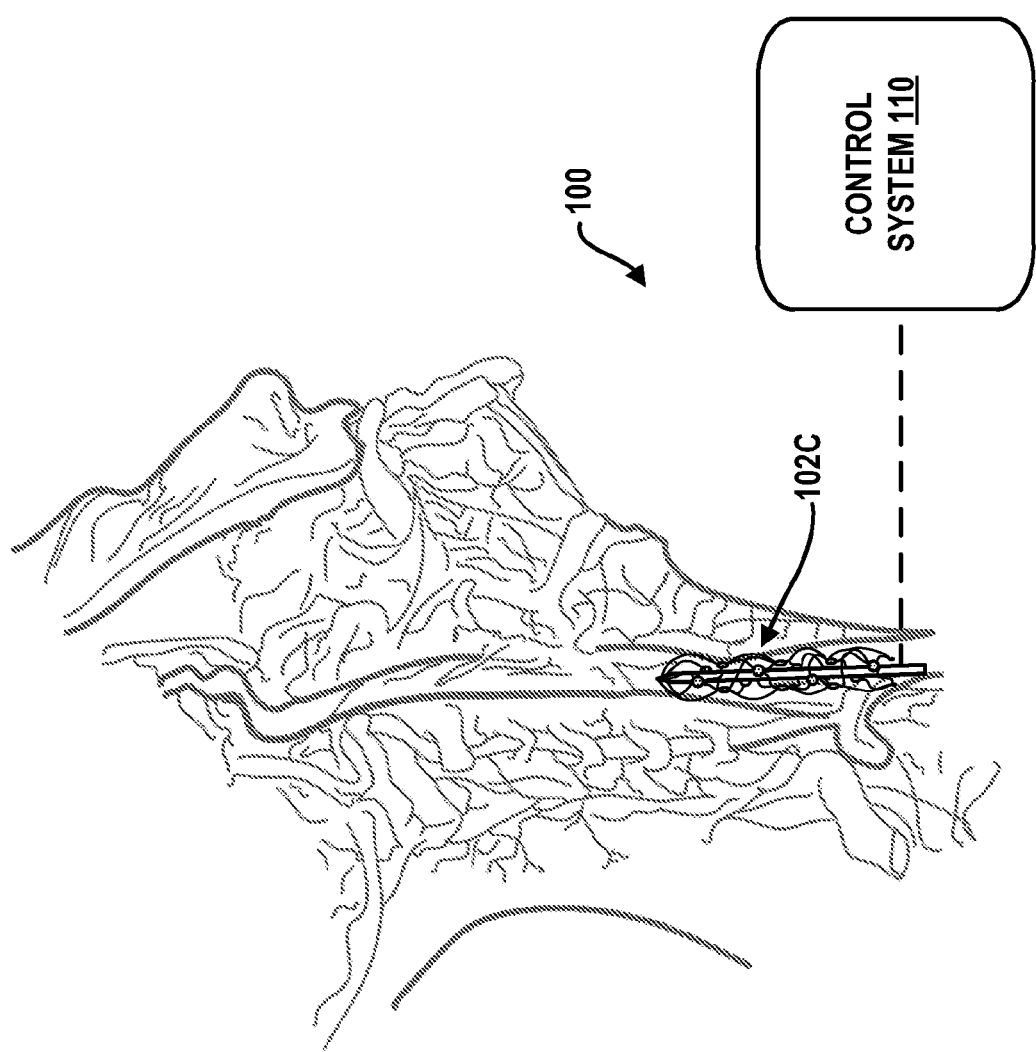
FIGS. 12A-12D are a series of simplified illustrations showing application of EFT treatment to various luminal structures by the EFT system of FIG. 1.
Figure 12C:
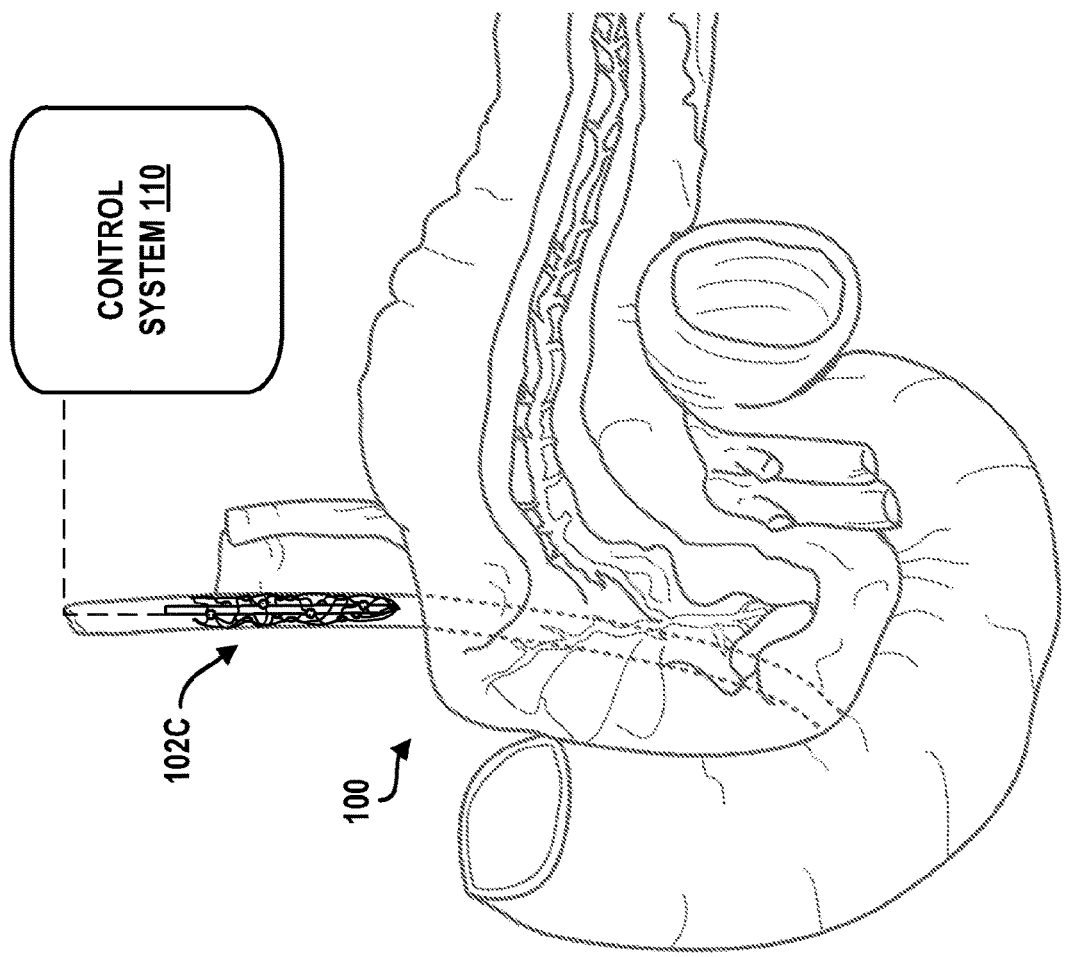

FIGS. 12A-12D illustrate an example for placement of implantable electrodes 102 of the implantable EFT system 100 relative to various luminal parenchymal structures. Intra-luminal applications are a broad but reproducible concept of an intra-luminal electrode 102C which can deliver a local electric field therapy either extra-luminally or intra-luminally. The intra-luminal electrode 102C can be utilized for intra-luminal metastasis prevention in the setting of a primary small-cell lung cancer or melanoma where the likelihood for cerebral metastasis is high, through implantation within the carotid artery bilaterally (FIG. 12A). The anticipated parameters for such applications are anticipated to fall within the stimulating waveform frequency range of 100 kHz-1 MHz. Effective treatment for the blood at a stimulating waveform frequency 150 kHz will result in permittivity of 5.03E+3 F/m and electrical conductivity of 7.06E−1 S/m based on empirical data.

Figure 12B:
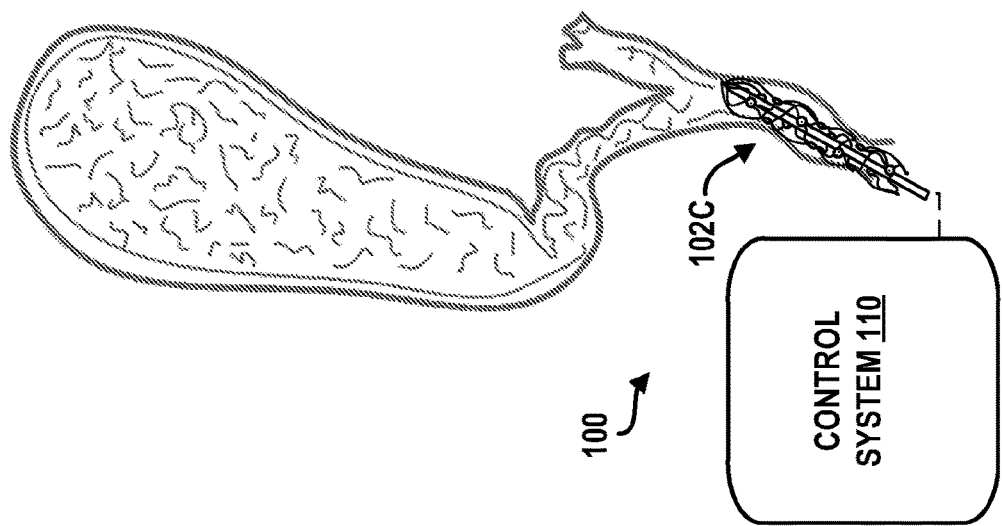
Figure 12D:
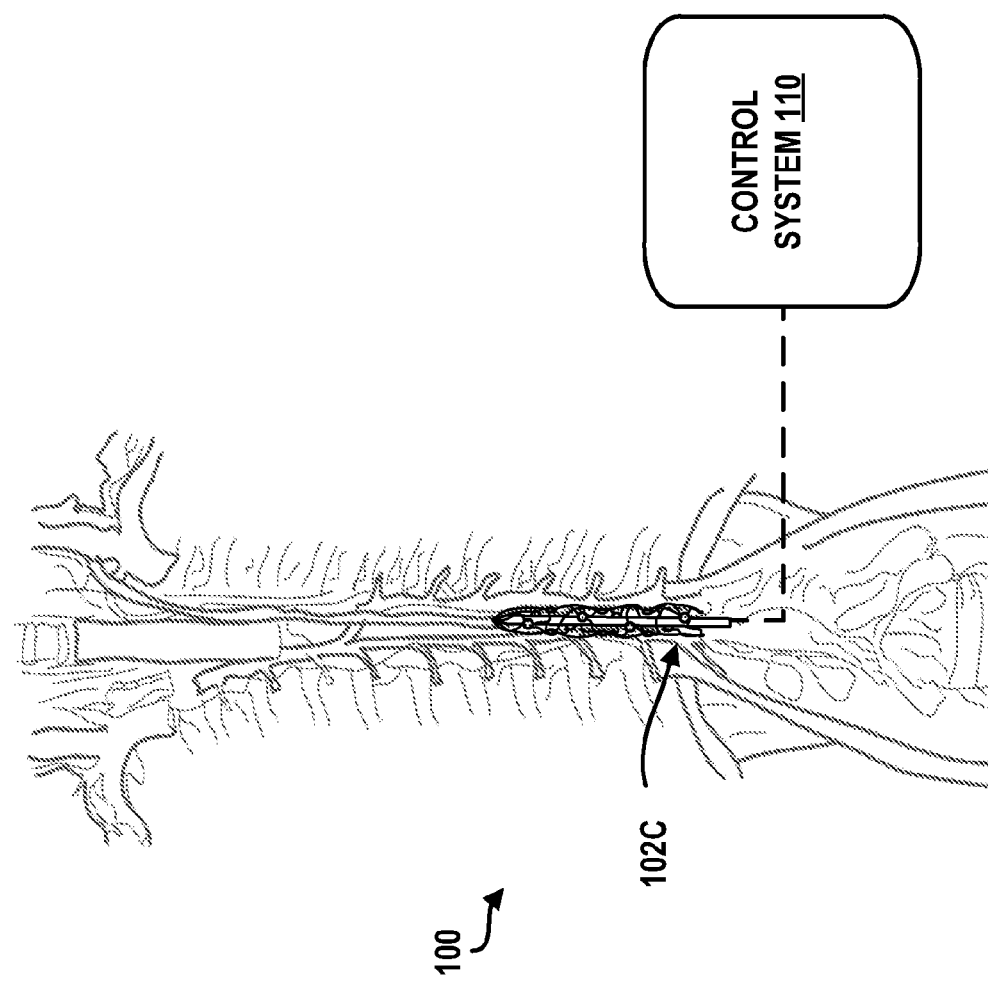

The stent-based electrode(s) provide a means of extra-luminal treatment of tumor spread involving the biliary tree such as cholangiocarcinoma (FIG. 12B). It may also be used as combined treatment for ensuring patency of such a lumen, as is necessary in some cases of pancreatic cancer (FIG. 12C), and also serving the purpose of delivering electric field therapy. The anticipated parameters for such applications are anticipated to fall within the stimulating waveform frequency range of 100 kHz-1 MHz. Effective treatment for the biliary tree at a stimulating waveform frequency of 150 kHz will result in permittivity of 1.05E+2 F/m and electrical conductivity of 9.00E−1 S/m based on empirical data.

An additional application is the placement of an intra-luminal stent-based electrode(s) within the thoracic duct (FIG. 12D, a major lymphatic channel draining lymph from a majority of the lower extremities and pelvic region) for the purposes of metastatic prevention. The anticipated parameters for such applications are anticipated to fall within the stimulating waveform frequency range of 100 kHz-1 MHz. Effective treatment for the lymphatic fluid at a stimulating waveform frequency of 150 kHz will result in permittivity of 9.16E+1 F/m and electrical conductivity of 5.90E−1 S/m based on empirical data.

Spinal Cord Example

Figure 13:
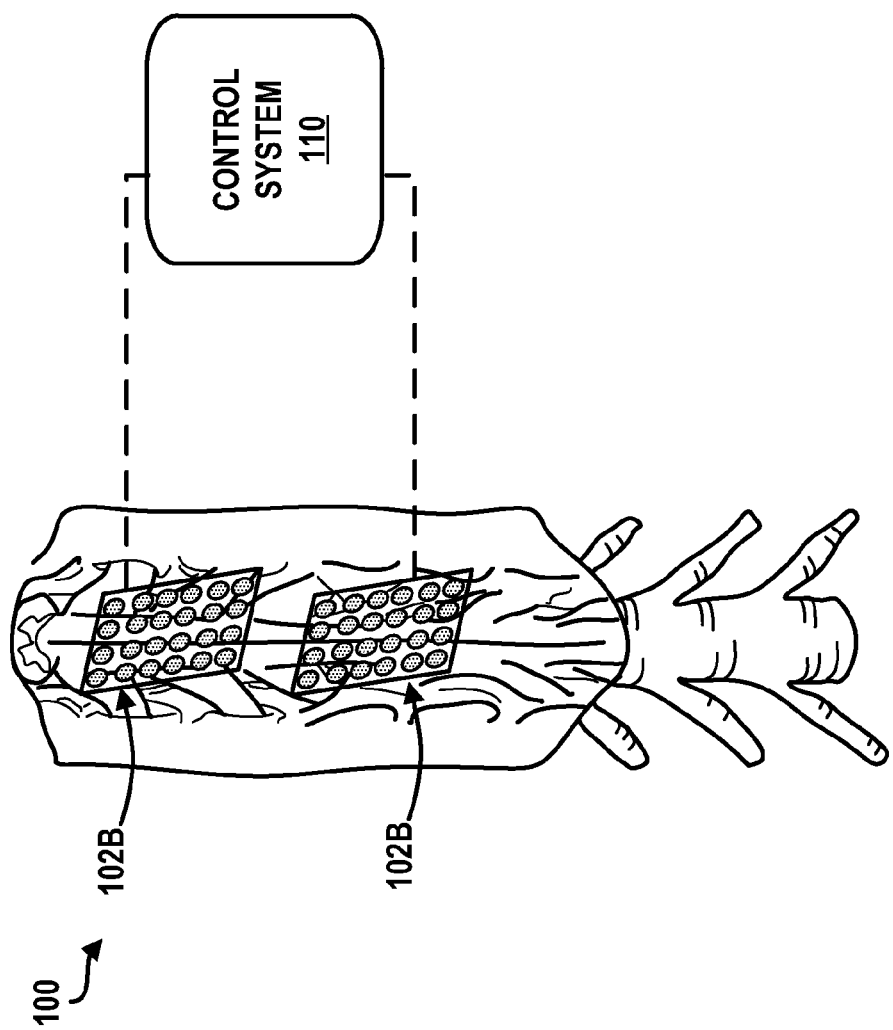
FIG. 13 is a simplified illustration showing application of EFT treatment to a spinal column by the EFT system of FIG. 1.

FIG. 13 illustrates an example for placement of implantable electrodes 102 of the implantable EFT system 100 relative to a spinal cord. This particular example demonstrates an intradural placement of implantable electrodes 102, however extra-dural placement has also been conceived. Spinal cord treatment can be accomplished with implanted extra-parenchymal electrodes 102B. The eloquent nature of the spinal cord prevents the safe use of tissue penetrating electrodes such as intra-parenchymal electrodes 102A. The treatment application to the region of the spinal cord is most appropriate for both intra- and extra-medullary spinal cord tumors. An example of spinal astrocytoma would be most appropriately treated with the application of alternating electric field therapy using an alternating sinusoidal waveform at a stimulating waveform frequency of 200 kHz alternating sinusoid waveform. Effective treatment for the spinal cord at a stimulating waveform frequency 200 kHz will result in permittivity of 9.16E+1 F/m and electrical conductivity of 5.90E−1 S/m based on empirical data.

A design of the extra-parenchymal electrodes 102B for the spinal cord including pre-cut perforations 106 (FIG. 1) to avoid infringing on the exiting spinal nerves provides an optimal treatment environment given the narrow shape of the spinal cord which will permit favorable phase-shifting electrode pairing opportunities across the spinal cord to enhance field strength and reduce power consumption.

Pulmonary Example

Figure 14:
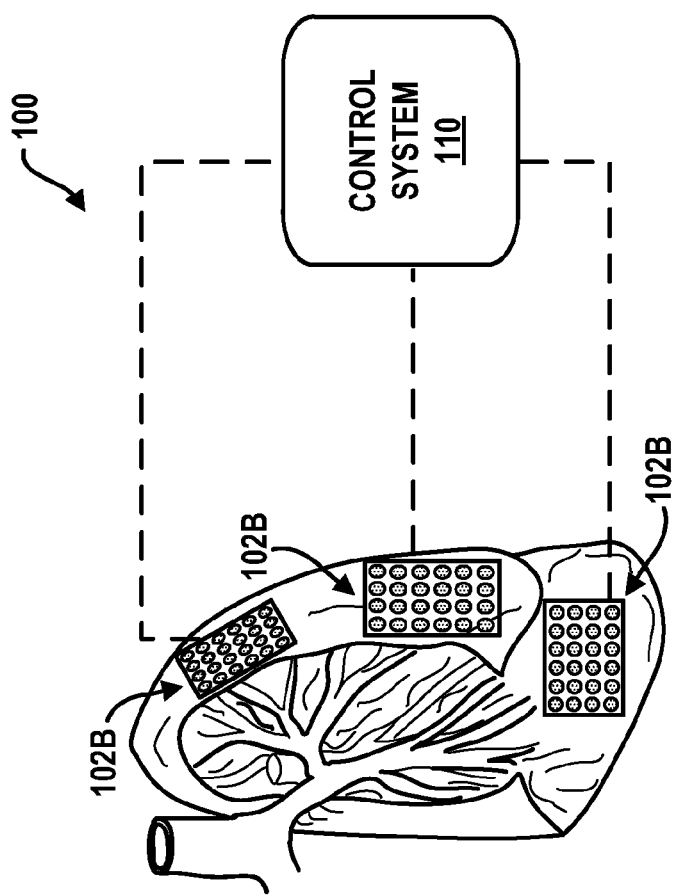
FIG. 14 is a simplified illustration showing application of EFT treatment to a lung by the EFT system of FIG. 1.

FIG. 14 illustrates an example for placement of implantable electrodes 102 of the implantable EFT system 100 relative to a lung. Pulmonary application of electric field therapy has the unique challenge of needing to maintain the pleural interface (parietal and visceral) along the pulmonary surface to ensure lung expansion and to avoid penetration of the pulmonary tissue to prevent pneumothorax generation. This necessitates the utilization of extra-parenchymal electrodes 102B or other forms of surface coverage electrodes along the surface of the region of interest. The anticipated parameters for such applications are anticipated to fall within the stimulating waveform frequency range of 100 kHz-1 MHz with the value of 150 kHz being most likely to provide the strongest impact on tumor growth. Effective treatment for the pulmonary tissue at a stimulating waveform frequency of 150 kHz will result in permittivity of 1.98E+3 F/m and electrical conductivity of 1.10E−1 S/m based on empirical data.

Process

Figure 15:
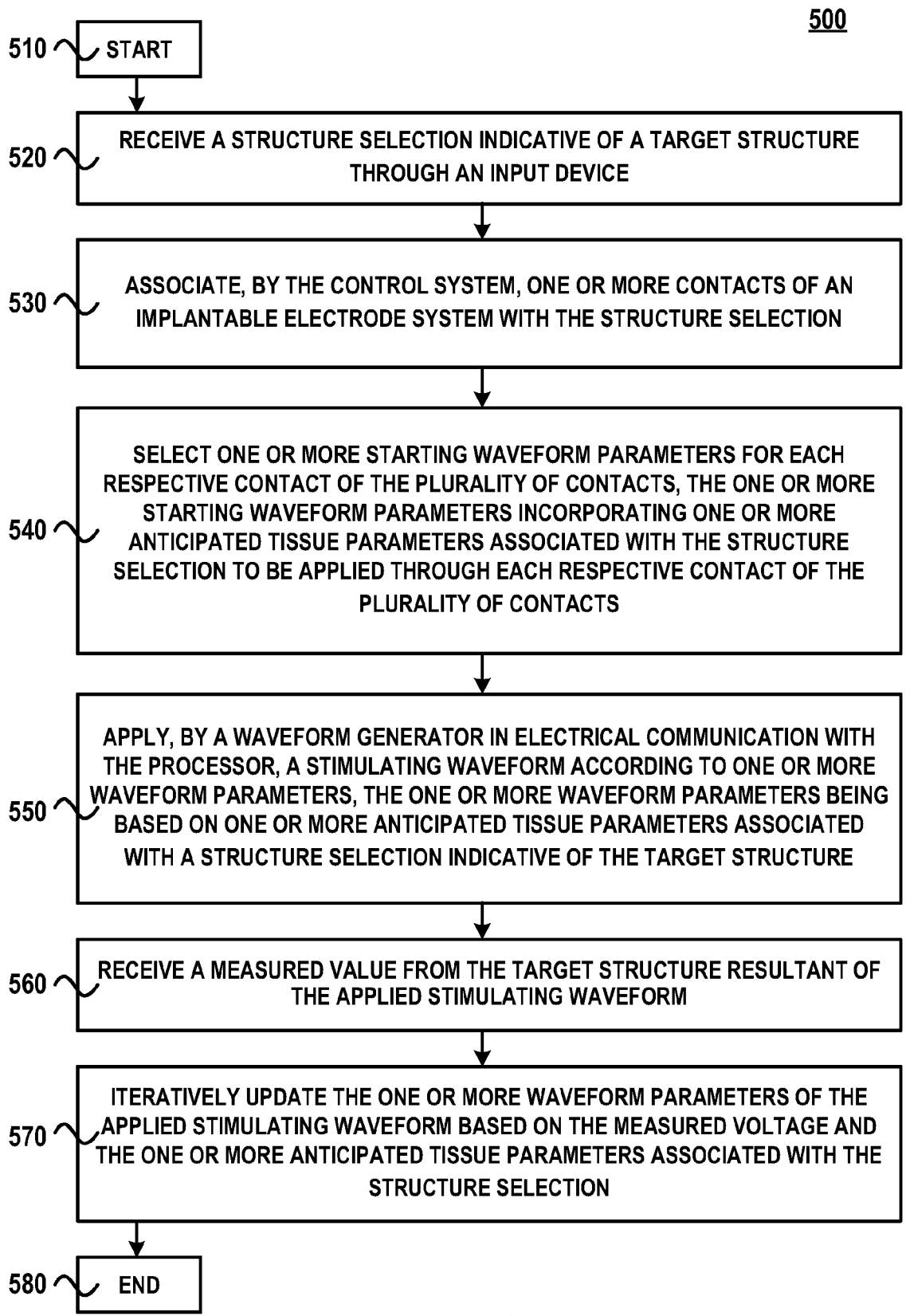
FIG. 15 is a process flow showing a method for feedback-modulated application of EFT by the EFT system of FIG. 1.

FIG. 15 illustrates a process flow 500 for application of EFT through the implantable EFT system with modulatory feedback based on a structure selection. Process flow 500 starts at block 510. At block 520, a processor receives one or more structure selection indicative of one or more target structures through an input device. At block 530, the processor and/or the control system of the implantable EFT system collectively associate one or more contacts of an implantable EFT system with the structure selection. At block 540, the processor selects one or more starting waveform parameters for each respective contact of the plurality of contacts of the implantable EFT system, the one or more starting waveform parameters incorporating one or more anticipated tissue parameters associated with each structure selection to be applied through each respective contact of the plurality of contacts of the implantable EFT system. At block 550, the implantable EFT system applies, by the waveform generator of the control system in electrical communication with the processor, a stimulating waveform according to one or more waveform parameters, the one or more waveform parameters being based on one or more anticipated tissue parameters associated with each structure selection indicative of the respective target structure. At block 560, the implantable EFT system receives, at a feedback module of the of the control system in electrical communication with the processor, a measured value from the target structure resultant of the applied stimulating waveform. At block 570, iteratively updates the one or more waveform parameters of the applied stimulating waveform based on the measured value and the one or more anticipated tissue parameters associated with the structure selection. Process flow 500 ends at block 580.

Computer-Implemented System

Figure 16:
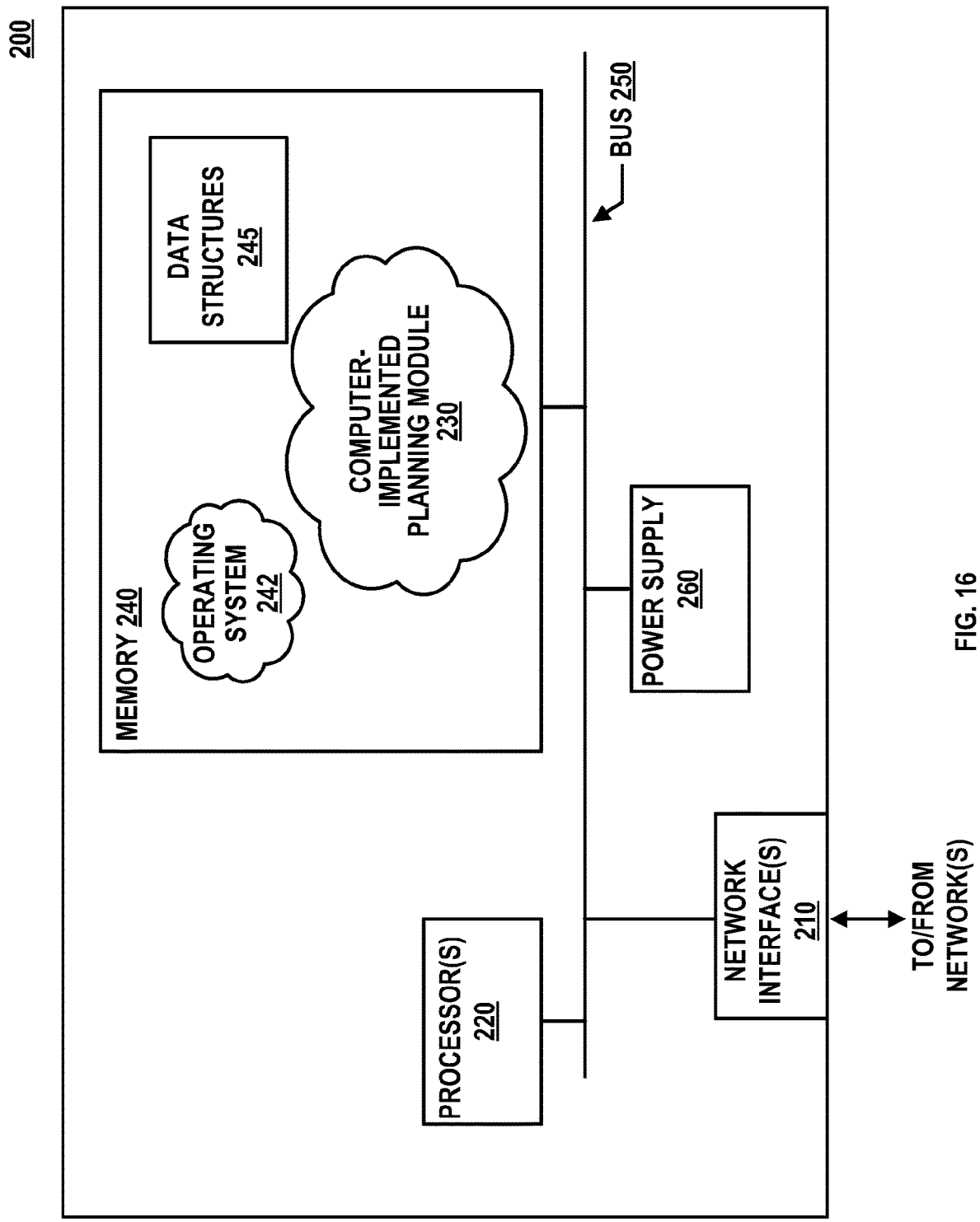
FIG. 16 is a simplified diagram showing an exemplary computing system for implementation of the EFT system of FIG. 1.

FIG. 16 is a schematic block diagram of an example device 200 that may be used with one or more embodiments described herein, e.g., as a component of implantable EFT system 100 and/or as computing device 200 shown in FIG. 1.

Device 200 comprises one or more network interfaces 210 (e.g., wired, wireless, PLC, etc.), at least one processor 220, and a memory 240 interconnected by a system bus 250, as well as a power supply 260 (e.g., battery, plug-in, etc.).

Network interface(s) 210 include the mechanical, electrical, and signaling circuitry for communicating data over the communication links coupled to a communication network.

Network interfaces 210 are configured to transmit and/or receive data using a variety of different communication protocols. As illustrated, the box representing network interfaces 210 is shown for simplicity, and it is appreciated that such interfaces may represent different types of network connections such as wireless and wired (physical) connections. Network interfaces 210 are shown separately from power supply 260, however it is appreciated that the interfaces that support PLC protocols may communicate through power supply 260 and/or may be an integral component coupled to power supply 260.

Memory 240 includes a plurality of storage locations that are addressable by processor 220 and network interfaces 210 for storing software programs and data structures associated with the embodiments described herein. In some embodiments, device 200 may have limited memory or no memory (e.g., no memory for storage other than for programs/processes operating on the device and associated caches). In a primary embodiment, the memory 240 comprises a non-transitory computer-readable medium with instructions stored thereon for execution by the processor.

Processor 220 comprises hardware elements or logic adapted to execute the software programs (e.g., instructions) and manipulate data structures 245. An operating system 242, portions of which are typically resident in memory 240 and executed by the processor, functionally organizes device 200 by, inter alia, invoking operations in support of software processes and/or services executing on the device. These software processes and/or services may include computer-implemented planning module 230 described herein. Note that while computer-implemented planning module 230 is illustrated in centralized memory 240, alternative embodiments provide for the process to be operated within the network interfaces 210, such as a component of a MAC layer, and/or as part of a distributed computing network environment.

It will be apparent to those skilled in the art that other processor and memory types, including various computer-readable media, may be used to store and execute program instructions pertaining to the techniques described herein. Also, while the description illustrates various processes, it is expressly contemplated that various processes may be embodied as modules or engines configured to operate in accordance with the techniques herein (e.g., according to the functionality of a similar process). In this context, the term module and engine may be interchangeable. In general, the term module or engine refers to model or an organization of interrelated software components/functions. Further, while the computer-implemented planning module 230 is shown as a standalone process, those skilled in the art will appreciate that this process may be executed as a routine or module within other processes.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system, comprising:
   an implantable electrode comprising a plurality of contacts and configured to apply a stimulating waveform to a target structure and receive a measured voltage from the target structure; and
   a processor in electrical communication with the plurality of contacts and a memory, the memory including instructions, which, when executed, cause the processor to:
   execute, by the processor, a planning module that assigns a stimulating role or a measuring role to a contact of the plurality of contacts of the implantable electrode based on a tumor region present within the target structure;
   apply, by a waveform generator in electrical communication with the processor, the stimulating waveform according to one or more waveform parameters, the one or more waveform parameters being based on one or more anticipated tissue parameters associated with a structure selection indicative of the target structure and based on the tumor region present within the target structure; and
   adjust, at the processor, an electric field magnitude throughout the target structure based on the measured value that is resultant of the stimulating waveform from the target structure.

2. The system of claim 1, wherein the memory further includes instructions, which, when executed, cause the processor to:
   iteratively update the one or more waveform parameters of the applied stimulating waveform based on the measured value and the one or more anticipated tissue parameters associated with the structure selection and based on the tumor region present within the target structure.

3. The system of claim 1, wherein the memory further includes instructions, which, when executed, cause the processor to:
   associate the structure selection with each respective contact of the plurality of contacts; and
   select one or more starting waveform parameters for each respective contact of the plurality of contacts, the one or more starting waveform parameters incorporating one or more anticipated tissue parameters associated with the structure selection and being selected based on the tumor region present within the target structure.

4. The system of claim 1, wherein the memory further includes instructions, which, when executed, cause the processor to:
   compare the measured value with an expected value for the associated structure selection; and
   compute one or more updated waveform parameters of the applied stimulating waveform using the one or more anticipated tissue parameters associated with the structure selection for the tumor region and a disparity between the measured value and the expected value.

5. The system of claim 1, wherein the memory further includes instructions, which, when executed, cause the processor to:
   display, at a display device in communication with the processor, a virtual space model representative of the target structure, the virtual space model including a modeled electrode object representative of the implantable electrode and including a tumor region associated with the target structure.

6. The system of claim 1, wherein the one or more anticipated tissue parameters associated with the structure selection indicative of the target structure includes at least one of:
   an anticipated permittivity of the target structure;
   an anticipated conductivity of the target structure; and/or
   an anticipated volume of the target structure.

7. The system of claim 6, wherein the structure selection indicative of the target structure includes a parenchymal sub-structure selection indicative of a sub-structure of the target structure.

8. The system of claim 6, wherein the structure selection indicative of the target structure includes a stroma structure selection indicative of an extra-parenchymal structure associated with the target structure.

9. The system of claim 1, wherein the implantable electrode is an extra-parenchymal electrode and wherein the plurality of contacts are configured to engage an external surface of the target structure.

10. The system of claim 1, wherein the implantable electrode is an intra-parenchymal electrode and wherein the plurality of contacts are configured to engage an interior of the target structure.

11. The system of claim 1, wherein the implantable electrode is an intra-luminal electrode and wherein the plurality of contacts are configured to engage an intra-luminal surface of the target structure.

12. A method, comprising:
executing, by a processor, a planning module that assigns a stimulating role or a measuring role to a contact of a plurality of contacts of an implantable electrode based on a tumor region present within a target structure;
applying, by an implantable electrode in electrical communication with a waveform generator, a stimulating waveform to the target structure according to one or more waveform parameters, the one or more waveform parameters being based on one or more anticipated tissue parameters associated with a structure selection indicative of the target structure and based on the tumor region present within the target structure; and
adjusting, at a processor in electrical communication with the implantable electrode, an electric field magnitude throughout the target structure based on a measured voltage that is resultant of the stimulating waveform from the target structure.

13. The method of claim 12, further comprising:
iteratively updating, by the processor in electrical communication with the waveform generator, the one or more waveform parameters of the applied stimulating waveform based on the measured voltage and the one or more anticipated tissue parameters associated with the structure selection and based on the tumor region present within the target structure.

14. The method of claim 12, further comprising:
associating, by the processor, the structure selection with each respective contact of a plurality of contacts of the implantable electrode; and
selecting, by the processor, one or more starting waveform parameters for each respective contact of the plurality of contacts, the one or more starting waveform parameters incorporating one or more anticipated tissue parameters associated with the structure selection and being selected based on the tumor region present within the target structure.

15. The method of claim 12, further comprising:
comparing, by the processor, the measured voltage with an expected value for the associated structure selection; and
computing, by the processor, one or more updated waveform parameters of the applied stimulating waveform using the one or more anticipated tissue parameters associated with the structure selection for the tumor region and a disparity between the measured value and the expected value.

16. The method of claim 12, further comprising:
receiving, at a user interface in communication with the processor, the structure selection indicative of the target structure.

17. The method of claim 16, further comprising at least one of:
receiving, at the user interface, a parenchymal sub-structure selection indicative of a parenchymal sub-structure of the target structure;
and/or receiving, at the user interface, a stroma structure selection indicative of a stroma structure associated with the target structure.

18. The method of claim 12, further comprising at least one of:
retrieving, from a parenchymal structure library in communication with the processor, the one or more anticipated tissue parameters associated with the structure selection indicative of the target structure including at least one of:
an anticipated permittivity of the target structure;
an anticipated conductivity of the target structure; and/or
an anticipated volume of the target structure.

19. The method of claim 12, further comprising:
displaying, at a display device in communication with the processor, a virtual space model representative of the target structure, the virtual space model including a modeled electrode object representative of the implantable electrode and including a tumor region associated with the target structure.

20. A non-transitory computer-readable medium having instructions stored therein and executable by a processor, wherein the instructions, when executed, cause the processor to:
execute a planning module that assigns a stimulating role or a measuring role to a contact of a plurality of contacts of an implantable electrode based on a tumor region present within a target structure;
apply, by the implantable electrode in electrical communication with a waveform generator and a processor, a stimulating waveform according to one or more waveform parameters to the target structure, the one or more waveform parameters being based on one or more anticipated tissue parameters associated with a structure selection indicative of the target structure and based on the tumor region present within the target structure; and
adjust, at a processor in electrical communication with the implantable electrode, an electric field magnitude throughout the target structure based on a measured voltage that is resultant of the stimulating waveform from the target structure.

21. The non-transitory computer-readable medium of claim 20, wherein the instructions, when executed, further cause the processor to:
iteratively update, by the processor in electrical communication with the waveform generator, the one or more waveform parameters of the stimulating waveform based on the measured voltage and the one or more anticipated tissue parameters associated with the structure selection and based on the tumor region present within the target structure.

22. The non-transitory computer-readable medium of claim 20, wherein the instructions, when executed, further cause the processor to:

associate, by the processor, the structure selection with each respective contact of a plurality of contacts of the implantable electrode; and select, by the processor, one or more starting waveform parameters for each respective contact of the plurality of contacts, the one or more starting waveform parameters incorporating one or more anticipated tissue parameters associated with the structure selection and being selected based on the tumor region present within the target structure.

23. The non-transitory computer-readable medium of claim 20, wherein the instructions, when executed, further cause the processor to:

compare, by the processor, the measured voltage with an expected value for the associated structure selection; and compute, by the processor, one or more updated waveform parameters of the applied stimulating waveform using the one or more anticipated tissue parameters associated with the structure selection for the tumor region and a disparity between the measured value and the expected value.

24. The non-transitory computer-readable medium of claim 20, wherein the instructions, when executed, further cause the processor to:

retrieve, from a parenchymal structure library stored on a non-transitory computer-readable medium in communication with the processor, the one or more anticipated tissue parameters associated with the structure selection indicative of the target structure including at least one of:

an anticipated permittivity of the target structure;

an anticipated conductivity of the target structure; and/or an anticipated volume of the target structure.

* * * * *